(12) United States Patent
Li et al.

(10) Patent No.: US 8,153,103 B2
(45) Date of Patent: Apr. 10, 2012

(54) CONJUGATES OF PHOTO-ACTIVATABLE DYES

(75) Inventors: Wen-Hong Li, Dallas, TX (US); Yan-Ming Guo, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 376 days.

(21) Appl. No.: 12/496,289

(22) Filed: Jul. 1, 2009

(65) Prior Publication Data

US 2010/0040554 A1    Feb. 18, 2010

Related U.S. Application Data

(60) Provisional application No. 61/133,695, filed on Jul. 1, 2008.

(51) Int. Cl.
*A61B 5/00* (2006.01)
*A61B 8/00* (2006.01)
*A61B 10/00* (2006.01)

(52) U.S. Cl. ...... 424/9.6; 424/1.11; 424/1.49; 424/1.65; 424/1.69; 424/1.73

(58) Field of Classification Search ............... 424/1.11, 424/1.49, 1.65, 1.69, 1.73, 1.81, 1.85, 1.89, 424/9.1, 9.2, 9.6; 549/200

See application file for complete search history.

(56) References Cited

U.S. PATENT DOCUMENTS 5,208,350 A * 5/1993 Bouma et al. .................. 549/289
7,304,168 B2 * 12/2007 Li et al. .......................... 549/289

OTHER PUBLICATIONS

Bao, Z., et al., Automated Cell Lineage Tracing in *Caenorhabditis elegans*, Proceeding, National Academy of Science, USA, 2006, 13:8, 2707-2712.
Bossinger, O., et al., Cell-Cell Communication in the Embryo of *Caenorhabditis elegans*, Developmental Biology, 1992, 151, 401-9.
Bossinger, O., et al., The Use of Fluorescent Marker Dyes for Studying Intercellular Communication in Nematode Embryos, Int J Dev Biol 1996, 40, 431-439.
Brenner, S., The Genetics of *Caenorhabditis elegans*, Genetics, 1974, 77, 71-94.
Dakin, K.; et al., Infrared LAMP: Two-photon uncaging and imaging of gap junctional communication in three Dimensions, Nature Methods, 2006, 3:12.
Dakin, K.; et al., LAMP, a New Imaging Assay of Gap Junctional Communication Unveils that Ca2+ Influx Inhibits Cell Coupling, Nature Methods, 2005, 2:1, 55-62.
Mitchison, T. J.; et al., "Caged Fluorescent Probes" Methods Enzymology, 1998, 291, 63-78.
Nagayama, S.; et al., In Vivo Simultaneous Tracing and Ca2+ Imaging of Local Neuronal Circuits, Neuron 2007, 53, 789-803.
Rozental, R., et al., "How to Close a Gap Junction Channel", Methods in Molecular Biology, Connexins methods and protocols; Humana Press: Totowa, 2001, p. 447-476.
Squirrell, J. M., et al., Long-term Two-photon Fluorescence Imaging of Mammalian Embryos Without Compromising Viability, Nat Biotechnoly, 1999, 17, 763-7.
Zhao, Y. et al., New Caged Coumarin Fluorophores with Extraordinary Uncaging Cross Sections Suitable for Biaological Imaging Application, J Am Chem Soc 2004, 126, 4653-63.
Takakusa, Hideo, et al., A Novel Design Method of Ratiometric Fluorescent Probes Based on Fluorescence Resonance Energy Transfer Switching by Spectra Overlap Integral, Chem. Eur. J. 2003, 9, No. 7, 1479-1485.
Albers, Aaron E., et al., A FRET-Based Approach to Ratiometric Fluorescence Detection of Hydrogen Peroxide, J. Am. Chem.Soc. 2006, 129, 9640-9641.
Zheng, Genhua, et al., Photoactivatable and Water Soluble FRET Dyes with High Uncaging Cross Section. J.Am. Chem.Soc.2007, 129, 10616, 10617.

* cited by examiner

*Primary Examiner* — D L Jones
(74) *Attorney, Agent, or Firm* — Jackson Walker L.L.P.

(57) ABSTRACT

A new class of photoactivatable dyes provides the ability to study cell-cell communication in live animals non-invasively with high spatiotemporal resolution. The compositions are made up of a macromolecule, a caging group, and a coumarin dye. Upon photolysis, the coumarin dye is released from the macromolecule caging group complex and is freely diffusible in cells and between cells. The compositions are retained in cells very well, having no observable side effects, no susceptibility to metabolism, and the ability to generate bright fluorescence signals after photolysis. Because of their high loading capacity and long cellular retention, they can be selectively uncaged in specific cells.

33 Claims, 17 Drawing Sheets a Type 1 Bioconjugates of Caged Probes (conventional)

Dextran-HCC-NPE → Dextran-HCC b Type 2 Bioconjugates of Caged Probes (new)

Dextran-CANPE-HCC → HCC

Dextran-CANPE-HCC

CONJUGATES OF PHOTO-ACTIVATABLE DYES

This application claims priority to U.S. Provisional Patent Application Ser. No. 61/133,695, entitled "Bioconjugates of Photo-Activatable Probes," filed on Jul. 1, 2008, the entire content of which is hereby incorporated by reference.

The present invention used in part funds from NIH National Institute of General Medical Sciences Grant Nos. R01 GM077593. The United States may have certain rights in the invention.

BACKGROUND

This present invention relates to caged dye compounds useful for imaging cell coupling, and particularly to a new bioconjugate of photoactivatable dye having outstanding photochemical and fluorescent properties.

Intercellular communication through gap junction channels is observed ubiquitously in multicellular organisms and is essential for many vital physiological processes including heart beating, labor, secretion, and neuronal communication. It has been recognized that cell-cell communication via gap junction channels plays important roles in cell specification, differentiation, and the orderly development of multicellular organisms. Over the past decades, there have been extensive efforts devoted to studying the regulation of junctional coupling in cultured cells, in heterologous expression systems such as *Xenopus* oocytes, and in isolated or reconstituted membranes. While these studies have generated a large amount of biochemical, biophysical and cellular biological insights on the property, assembly, trafficking, and regulation of gap junction channels, relatively fewer studies have been designed to extend these investigations into living organisms to address the physiological implications or consequences of these insights.

The paucity of in vivo data is due, at least in part, to the fact that there does not yet exist a non-invasive and sensitive assay to examine the distribution, strength, and the dynamics of cell coupling in living organisms. Such a technique would be tremendously useful to track junctional coupling in vivo, to address how physiological changes affect cell coupling, and to correlate how changes in cell-cell communication modulate biological responses or animal behavior. To gain further insights into the developmental significance of gap junction coupling, it would be desirable to construct a high resolution communication map which marks the occurrence, the strength, and the dynamics of junctional coupling with sufficient resolution over the course of development.

To study the regulation and physiological functions of cell-cell communication in vivo, major technological advancements are needed in at least two areas: new imaging methods to follow the dynamics of cell coupling in living animals, and new reagents to specifically modulate cellular junctional coupling strength in physiological preparations. In order to establish functional correlation between cell coupling and physiology or behavior in living animals, these techniques need to be minimally invasive, yet are capable of tracking or altering the dynamics of gap junction coupling with high spatiotemporal resolution over the course of a physiological measurement or a behavioral task.

Small and photo-activatable fluorophores are powerful probes for imaging gap junction coupling (Dakin et al., 2005). However, for in vivo applications, these probes are limited in two aspects: poor cellular loading and short cellular retention time. Microinjection of fluorescent tracers has been used for many years to probe cell coupling in tissues. The method is invasive, limited to a few cells, and may severely perturb biological functions or normal development.

Bossinger and Schierenberg previously examined dye transfer in *C. elegans* embryos by microinjection and iontophoresis of Lucifer Yellow dye and concluded that from the 4-cell stage all blastomeres are well coupled, and that restricted dye diffusion does not start until P4 and D cells are born (Bossinger et al., 1992). The failure to identify the transient coupling domains in early developing embryos could be due to several technical limitations of microinjection, including low temporal resolution or cell damage, poor quantification of dye transfer kinetics or coupling strength, and difficulty of reliably injecting the dye into a cell at precise moments of development or cell cycle. In addition, Lucifer Yellow binds strongly to yolk granules in early *C. elegans* embryos (Bossinger et al., 1992 and 1996). This further complicates the interpretation of dye diffusion data and diminishes the accuracy and sensitivity of measuring the rate of cell-cell dye transfer.

Local activation of molecular fluorescent probes ("LAMP") is one alternative to microinjection of fluorescent tracers. However, there are several challenges in adapting the LAMP technique to study gap junction coupling in vivo. First, cellular uptake of fluorescent dyes containing AM esters is generally poor in living organisms. The problem is more severe when we need to load interior cells away from the body surface. Second, synthetic organic molecules of low molecular weights, once being delivered into the cytosol, tend to slowly leak out of cells or become compartmentized in cellular organelles. This phenomenon makes it difficult to image small organic dyes over an extended period of time. Third, to generate robust fluorescence signals for the in vivo imaging, we need to have sufficient concentrations of caged probes in cells. These probes thus need to be chemically and metabolically stable, and should cause little toxicity or side effects on the labeled animals.

SUMMARY

One aspect of the current invention pertains to a new class of conjugates of caged photoactivatable dyes, including dextran-CANPE-HCC, for imaging cell coupling in small model organisms. In vitro, the compounds show outstanding photochemical and fluorescent properties. In the nematode *C. elegans*, dextran-CANPE-HCC is retained in cells throughout development after being delivered into *oocytes*.

In particular, the current invention pertains to conjugates of photoactivatable dyes that are made up of a macromolecular carrier, a bifunctional photolabile protecting group, and a coumarin fluorophore. The macromolecular carrier is preferably a biomolecule and is most preferably dextran. The bifunctional photolabile protecting group can be any caging group that will release the coumarin fluorophore after photolysis. Preferably, the protecting group is 1-(4-carbamoyl-2-nitrophenyl)ethyl.

One aspect of the present invention is a composition having the following general structure:

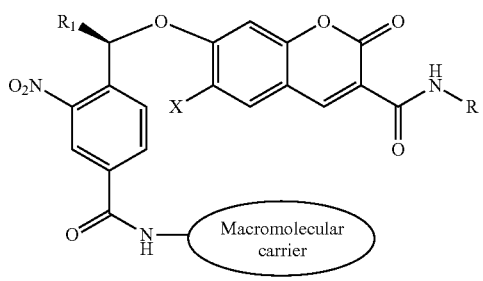

In one preferred embodiment, the composition has the structure shown below:

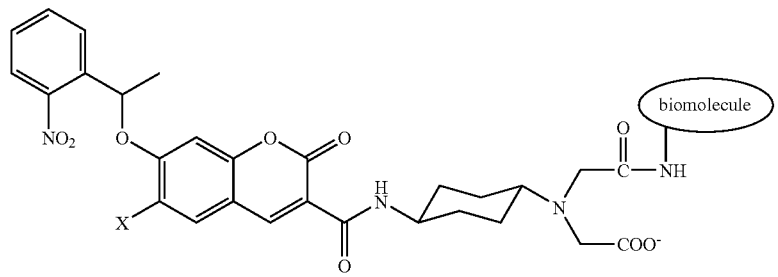

In another preferred embodiment, the composition includes bioconjugates of photoactivatable dyes that are dextran-CANPE-HCC, having the structure shown below:

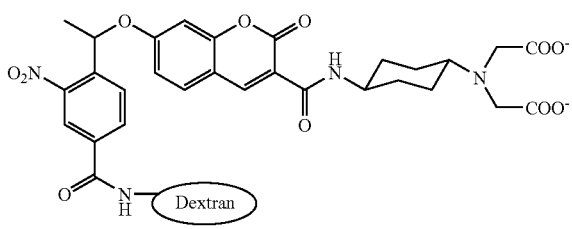

Effective methods for examining gap junction coupling in intact living cells include the photo-uncaging and fluorescence imaging techniques LAMP (i.e., local activation of molecular fluorescent probes) and infrared-LAMP, for measuring cell-cell dye transfer kinetics in cultured cells or in dissected tissues (Dakin et al., 2005 and 2006). These methods involve loading cells with a caged and membrane permeable coumarin dye, NPE-HCCC2/AM (Zhao et al., 2004). NPE-HCCC2/AM is a neutral and lipophilic molecule that can cross cell membranes by passive diffusion. Once inside cells, cellular esterases hydrolyze the AM ester to generate NPE-HCCC2, a charged and hydrophilic molecule which becomes trapped inside cells. Photolysis of NPE caging group produces HCCC2, a brightly fluorescent coumarin dye (molecular weight 450) which can diffuse through gap junction channels. Subsequent fluorescence imaging provides dynamic and quantitative information on cell junctional coupling. The LAMP technique is suitable for assaying cell coupling in cultured cells and in dissected tissues. However, its application in living organisms is limited because the cellular loading efficiency of NPE-HCCC2/AM is poor, especially for those cells that are away from the surface.

A new class of bioconjugates of photo-activatable dyes, including dextran-CANPE-HCC, have been developed for imaging cell coupling in living animals. HCC is 7-hydroxy-coumarin 3-carboxamide, and CANPE is 1-(4-carbamoyl-2-nitrophenyl)ethyl. In dextran-CANPE-HCC, a coumarin dye (HCC) is linked to the dextran carrier through a bifunctional photolabile protecting group or cage, CANPE. Upon photolysis, the coumarin fluorophore is released from the dextran-cage conjugate and becomes freely diffusible in cells. Extending the LAMP technique to assay cell coupling in living animals using the new class of bioconjugates of photo-activatable dyes circumvents two problems: poor dye loading and short cellular retention of small chemical probes in vivo. One member of this new class of bioconjugates, dextran-CANPE-HCC, exhibits outstanding photochemical and fluorescent properties, including very low background signal, high fluorescence contrast enhancement after uncaging, and high photolytic efficiency by both UV and two photon excitation. In addition, the probe is chemically and metabolically stable in cells, and causes little toxicity.

Both adults and developing embryos of model organisms are suitable biological subjects for studying gap junction coupling. Because of its limited cell number, *C. elegans* represents an attractive system to achieve this ambitious goal. After injecting dextran-CANPE-HCC into *C. elegans* adult hermaphrodites, the compound is retained in cells very well throughout the embryonic development and carried into hatched worms. The compound has no observable side effects on worm development. It also resists metabolism and generates bright fluorescence signals upon photolysis. Its photolyzed product, HCC fluorophore, appears to be inert to cytoplasmic constituents including yolk granules, and diffuses rapidly in cells of *C. elegans*. Moreover, by comparison with the traditional type I bioconjugates of caged fluorophores, carrier molecules of type II bioconjugates can be heavily labeled with caged dyes without showing self-quenching. This high payload maximizes the efficiency of probe delivery for a given amount of carrier molecules.

Characterization of the pattern of junctional cell coupling in developing *C. elegans* embryos is possible using the new class of bioconjugates of photo-activatable dyes, revealing a dramatic remodeling of cell coupling among early blastomeres even prior to the 4-cell stage with the germ line blastomere quickly becoming poorly coupled from somatic cells. Because of the high loading capacity and long cellular retention of dextran-CANPE-HCC, the probe can be uncaged in specific cells in hatched larvae to generate bright fluorescence labeling. This provides the ability to study cell-cell communication in live animals non-invasively with high spatiotempolal resolution.

DETAILED DESCRIPTION OF THE PREFERRED EMBODIMENTS

Figure 1:
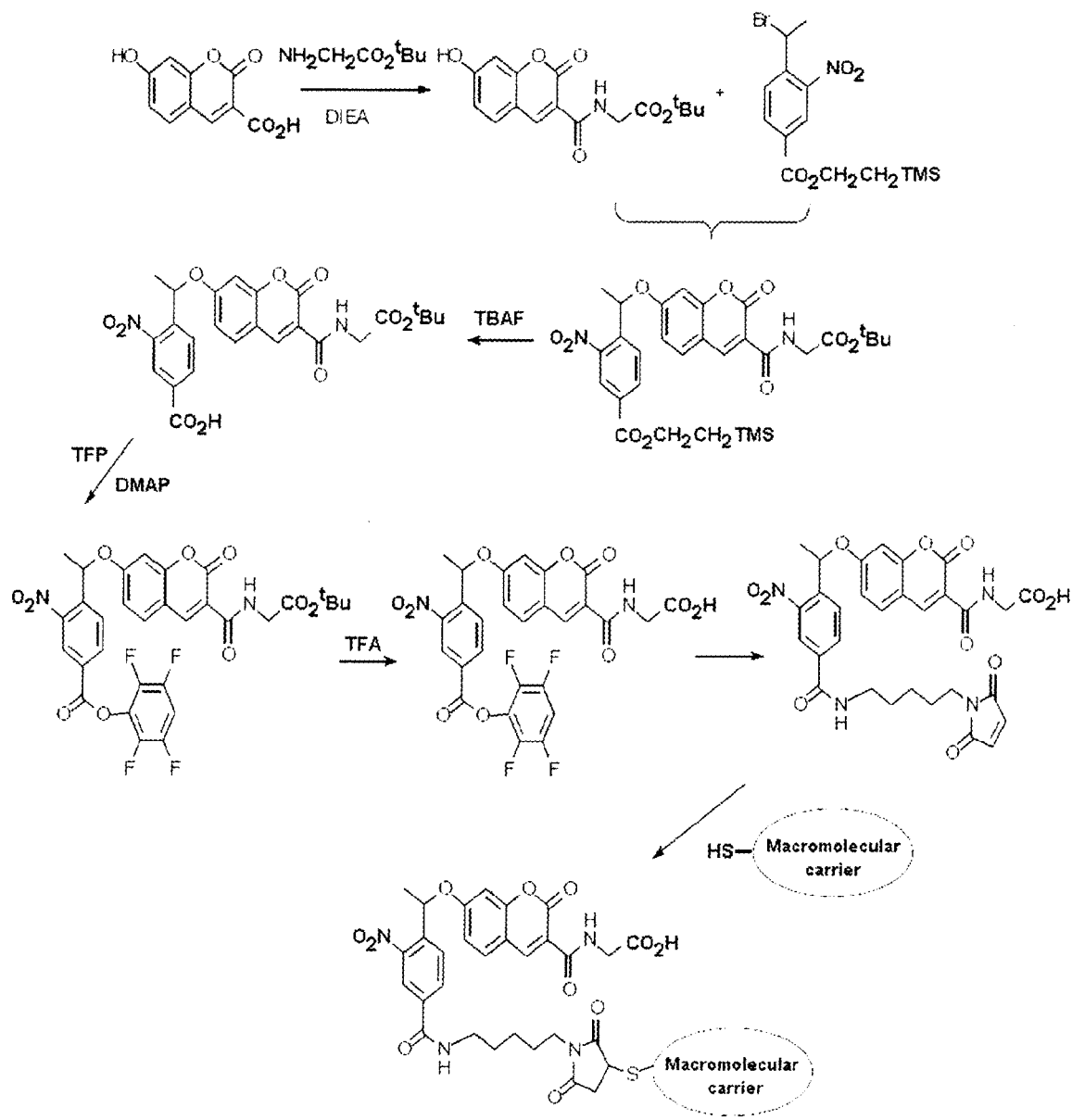
FIG. 1 shows a scheme outlining the synthesis of a bioconjugate through reacting with a thiol group on a macromolecular carrier.

One aspect of the present invention is a composition comprising a macromolecular carrier, a protecting group, and a coumarin fluorophore, and having the following general structure:

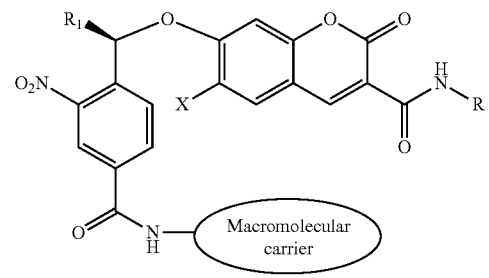

where

X can be H, F, Cl, or Br;

$R_1$ can be H or $CH_3$.

R can be up to 20 amino acids either in D or L configuration or their derivatives, any linear or branched alkyl chains up to 20 carbon atoms, peptides, oligonucleotides (natural or synthetic analogues including 2-methoxy RNA, locked nucleic acids, PNA, and others) containing amino groups at either 5' or 3' terminal, agonists or antagonists of cell receptors, therapeutic drugs, neurotransmitters, any molecules containing amino or carboxylate groups that serve as reactive sites for conjugation with 7-hydroxy-coumarin 3-carboxylate, or a combination thereof; and the macromolecular carrier can be proteins, antibodies, dextran amines, polylysine, polyethylene glycol, dendrimers, nanoparticles, quantum dots, any macromolecules containing amino or thiol groups that serve as reactive sites for conjugation with the protecting group, or a combination thereof.

In preferred embodiments, the protecting group is 1-(4-carbamoyl-2-nitrophenyl)ethyl, and the coumarin fluorophore is 7-hydroxycoumarin 3-carboxamide.

Generally, the R group and the macromolecular carrier can be any of a number of molecules that a person skilled in the art would understand to be suitable for the compositions. The composition must be chemically and metabolically stable and must be capable of uptake by cells. After uncaging, the coumarin fluorophore must also remain stable and produce a robust fluorescence. Many different R groups and macromolecular carriers can contribute to these properties, as those skilled in the art would understand.

The term "derivatives" of amino acids is a commonly understood term that refers to any amino acid molecules that have been modified, such as by the addition of substituents.

Examples include catecholamines, which are derivatives of the amino acid tyrosine, and serotonin and melatonin, which are both derivatives of tryptophan.

The term "peptides" is a commonly understood term that refers to polymers made up of amino acids or their derivatives. Peptides typically contain 50 amino acids or less.

The term "oligonucleotides" is a commonly understood term that refers to polymers of nucleic acids. Oligonucleotides typically contain 20 nucleic acids or less. The oligonucleotides can be natural or synthetic analogues. Examples include 2-methoxy RNA, locked nucleic acids ("LNA"), which are modified RNA molecules also referred to as inaccessible RNA, peptide nucleic acids ("PNA"), which are synthesized molecules having a backbone composed of repeating N-(2-aminoethyl)-glycine units linked by peptide bonds, and others. The oligonucleotides can also contain amino groups at either the 5' or 3' terminal.

The term "agonists" of cell receptors is a commonly understood term that refers to any ligands or drugs that bind to and positively or negatively alter the activity of a cell receptor. Examples include drugs such as morphine or buspirone.

The term "antagonists" of cell receptors is a commonly understood term that refers to any ligands or drugs that bind to a cell receptor and block or dampen an agonist-mediated response. Examples include cyclothiazide and memantine.

The term "therapeutic drugs" is a commonly understood term that refers to any drugs or pharmaceutical products typically considered to have a therapeutic effect on a subject for any condition.

The term "neurotransmitters" is a commonly understood term that refers to a variety of molecules, including amino acids, monoamines, and peptides, that relay, amplify, and modulate signals between neurons and other cells. Examples include glutamate, epinephrine, and acetylcholine.

The phrase "amino or carboxylate groups that serve as reactive sites for conjugation with 7-hydroxy-coumarin 3-carboxylate" refers to the amino group —$NH_2$ or the carboxylate group —COO, both of which are reactive sites that conjugate with 7-hydroxy-coumarin 3-carboxylate.

The term "antibodies" is a commonly understood term that refers to proteins used by the immune system to identify and neutralize foreign objects, such as bacteria and viruses.

The term "dextran amines" is a commonly understood term that refers to amines conjugated with dextran that can be tagged with fluorescent labels and used for tracing.

The term "polylysine" is a commonly understood term that refers to a polypeptide of the amino acid lysine.

The term "polyethylene glycol" is a commonly understood term that refers to an oligomer or polymer of ethylene oxide.

The term "dendrimers" is a commonly understood term that refers to certain repeatedly branched molecules having a high density, including polyphenylene dendrimers.

The term "nanoparticles" is a commonly understood term that refers to particles between 1 and 100 nm in size.

The term "quantum dots" is a commonly understood term that refers to semiconductors having unique properties between those of bulk semiconductors and discrete molecules.

The term "macromolecules containing amino or thiol groups that serve as reactive sites for conjugation with the protecting group" refers to any macromolecules containing the amino group —$NH_2$ or the thiol group —SH, both of which are reactive sites that will conjugate with the protecting group.

Another aspect of the present invention can be generalized according to the following scheme:

wherein the molecules are defined as above in [0033]. This scheme shows the release of the coumarin fluorophore after two photon or UV uncaging.

In one preferred embodiment, the composition has the structure shown below:

where X is H, F, Cl, or Br and the biomolecule is a protein, antibody, dextran amine, polylysine, polyethylene glycol, dendrimer, nanoparticle, quantum dot, any macromolecules containing amino or thiol groups that serve as reactive sites for conjugation with the protecting group, or a combination thereof.

In one preferred embodiment, the composition includes bioconjugates of photoactivatable dyes that are dextran-CANPE-HCC, having the structure shown below:

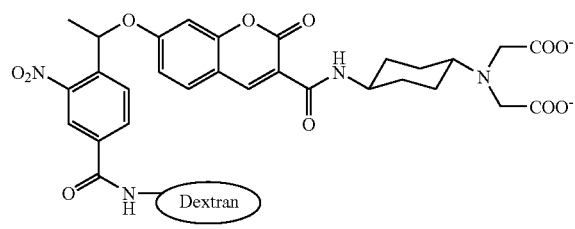

These compositions are useful for a variety of purposes. In each case, the general method is similar. The compositions are injected into cells in a region of interest, then, after the desired amount of time, light is applied to the cells, and, if desired, their progeny, and the resulting region of fluorescence is observed. This method can be used to observe cell-cell coupling and cell-cell communication in a living animal, to observe patterns of junctional cell coupling in cells of interest, to observe cell-cell coupling and cell-cell communications in developing embryos and young animals produced by adult parent animals, for comparing the coupling strength between pairs of coupled cells, for tracing cell lineage, and for tracking molecular movements in cells. This can be accomplished by both UV and two photon uncaging. In two photon uncaging, light of a first wavelength is applied first, followed by light of a second wavelength.

The scheme shown in FIG. 1 outlines the synthesis of one example of the composition, a bioconjugate, through a reaction with a thiol group on a macromolecular carrier.

Figure 2:
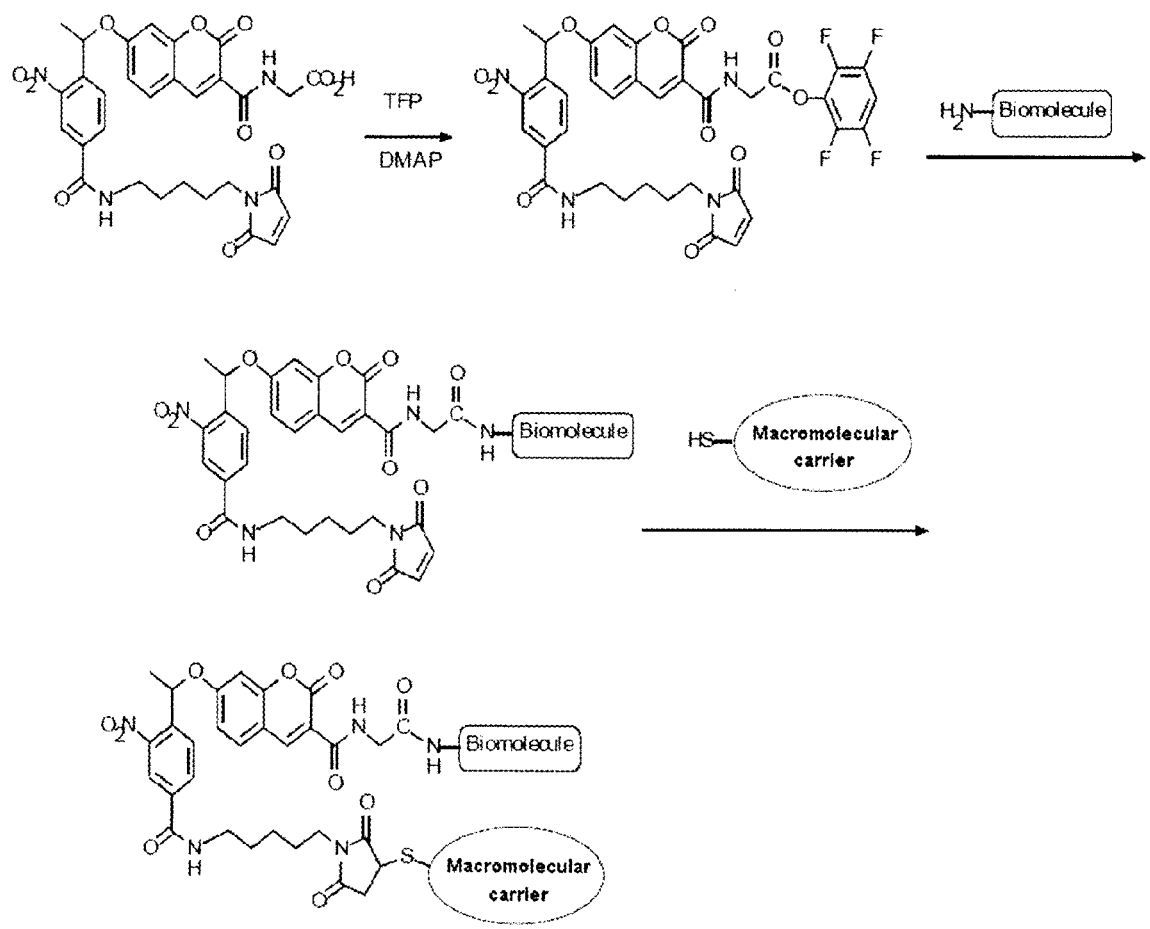
FIG. 2 shows a scheme outlining the synthesis of a bioconjugate through reacting with a thiol group on a macromolecule carrier, and through reacting with an amino group on a biomolecule.

The scheme shown in FIG. 2 outlines the synthesis of another example of the composition, a bioconjugate, through a reaction with a thiol group on a macromolecule carrier, and through reacting with an amino group on a biomolecule.

Without wanting to be bound by theory, the early separation of germ line precursor cells from the somatic cells may suggest a unique cytoplasmic characteristic important for maintaining germ line potential, or the need to exclude the morphogens that direct somatic cell differentiation. Future challenges are to identify endogenous molecules that pass through innexin channels, and to illustrate what permissive or instructive information they carry to set up signaling networks through gap junction channels.

The dramatic remodeling of the coupling pattern during early development also suggests that embryos may rapidly adjust cellular coupling strength as part of their developmental program. At 20° C., the entire 4-cell stage only lasts for about 10 minutes, during which EMS and P2 cells maintains gap junction coupling for several minutes in the early 4-cell stage. This transient coupling behavior has been observed in other organisms, yet with longer coupling duration from hours to a day. In Daphnia, the growth cone of optic fibers from one ommatidium forms gap junction channels with the neuroblasts in the optic lamina. This interaction is transient but always occurs the same for a particular cell hours before the onset of synaptogenesis. In developing leech embryos, axonal projections extend and gap junction channels form between adjacent anterior pagoda neurons before axons retract. Such temporary junctional communication in the developing nervous systems has been proposed to play a role in controlling neurogenesis and in the formation of neural circuits. Combining the LAMP assay with this new class of bioconjugates of caged fluorophores is likely to reveal other transient cell couplings during development. In addition, by using multi-color imaging and two photon uncaging and imaging techniques, the dynamics of gap junction coupling can be correlated with other biochemical or cellular processes in three dimensions. Such studies may reveal the timing and the interaction of cell-cell communication with other cellular events, which in turn may offer insights into the role of cell coupling in development.

Since the composition, and especially dextran-CANPE-HCC, is well retained in cells, and because it resists metabolic degradation throughout embryonic development, this permits imaging cell coupling in living worms after the labeled embryos hatch. A robust fluorescence signal can be generated by uncaging dextran-CANPE-HCC in the stage L1 and L2 larvae. By this time, the development of the nervous system, the alimentary system, and several tissues including muscles and hypodermal cells is finished or nearly complete, so the coupling dynamics can be characterized in many functional systems of wild type animals or mutants with defects in gap junction communication. Recent studies have shown that disrupted innexin expression or function can have profound effects on the development or on worms' physiology. The probes and techniques described here can be used to determine where, when, and to what extent, cell coupling is altered in these mutants. Besides C. elegans, other small organisms such as zebrafish, flies, and several marine species are also appropriate models for studying gap junction coupling. Since embryos of these animals only undergo a modest expansion in size during development, dextran-CANPE-HCC and other examples of the composition may also be applied similarly to these systems to study cell coupling over an extended period of time. To utilize the probe to track gap junction communication in mammalian systems, local electroporation (Nagayama et al., 2007) may serve as an alternative approach to deliver dextran-dye conjugates to cells of living mammals to enable long term imaging.

In addition to photoactivatable fluorophores the concept of type II bioconjugates of caged probes can also be extended to other molecules including second messengers, antisense oligonucleotides, agonists or antagonists of cellular receptors or ion channels, and others. Macromolecular conjugates of these bioactive molecules linked through appropriate caging groups would likewise have prolonged cellular retention time. This would allow non-invasive perturbing of cell signaling or biochemistry with high spatiotemporal resolution in living animals over a period of time and with amplification due to multiple side groups per dextran. Such techniques will undoubtedly offer new opportunities to investigate the organization, interaction, and timing of a variety of biochemical events in vivo, and to address their biological functions.

C. elegans has long been used as a model system to address fundamental questions in developmental biology, neurobiology and behavioral biology. The organism remains completely transparent at all stages of development and is thus ideal for optical imaging. The relatively small number of cells (about 560 cells in the first larval stage, and about 1000 in the adult), invariant cell lineage, and the availability of the entire cellular architecture by serial section electron microscopy provide unique resources and advantages for tracking cell-cell communication networks during development and in adults.

As an invertebrate, C. elegans express innexins rather than connexins. The genome sequencing project has identified 25 innexin genes in C. elegans. More recently, innexin-like genes named pannexins were discovered in mammals. Although innexins or pannexins share no significant sequence similarity with connexins, the overall topologies of these three classes of proteins are remarkably alike, and they have been suggested to play roles in mediating cell-cell communication. Currently little is known about the functions of pannexins in vivo. Studying cell-cell communication through innexin channels in C. elegans may shed light on the regulation and function of pannexins. Since the composition, including dextran-CANPE-HCC, is chemically and metabolically stable, labeled animals will show a very bright signal upon photoactivation even after they hatch. This offers the opportunity to examine cell coupling in living worms non-invasively.

In the examples below, the dynamics of dye transfer from the 2-cell to the late 4-cell stage were systematically characterized, and the coupling pattern near the embryo posterior from the 8-cell to the 28-cell stage was examined. The imaging experiments reveal a very dynamic pattern of selective cell coupling during early development. Strong cell coupling is first seen between AB daughter cells at the 3-cell stage. When P1 daughter cells finish cytokinesis, they also establish strong coupling, so an early 4-cell embryo has two communication compartments: one contains ABa and ABp, and the other contains EMS and P2. However, these two distinct coupling domains are only present transiently. By the late 4-cell stage, ABa, ABp, and EMS form a strong communication compartment which is poorly connected with the P2 cell, the germline precursor. The weak communication between P2 and other somatic cells persists during subsequent cell divisions. When the embryo develops to the 28-cell stage, all six founder cells, AB, MS, E, C, D, and P4, are born. Among them and their daughter cells, D and P4 cells appear to be the only two cells that are separated from the somatic communication compartment.

This high resolution map of cell-cell coupling developed as a result of using the current bioconjugates offers much more dynamic and detailed information than what was known previously about cell communication during the early embryogenesis of C. elegans.

Figure 3:
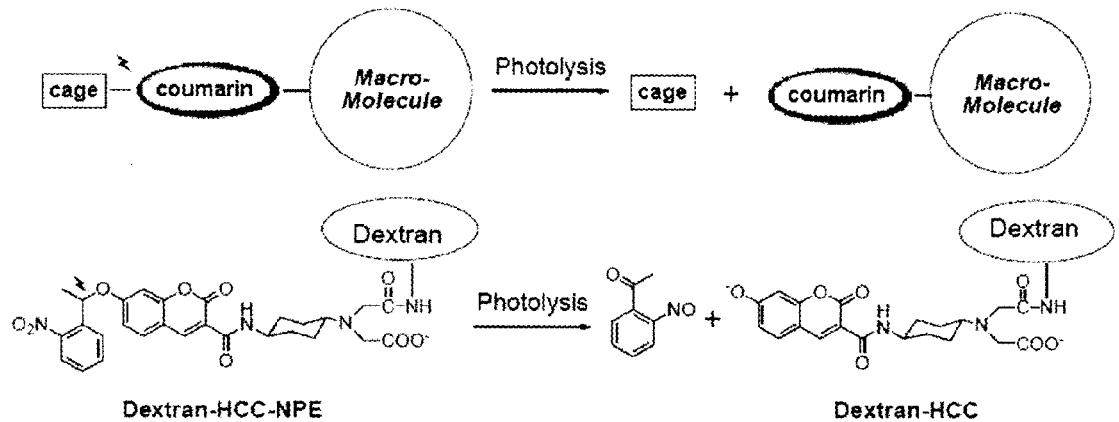
FIG. 3 shows a comparison of (a) conventional bioconjugates of caged probes with (b) the current new class of bioconjugates of caged probes.
Figure 3:
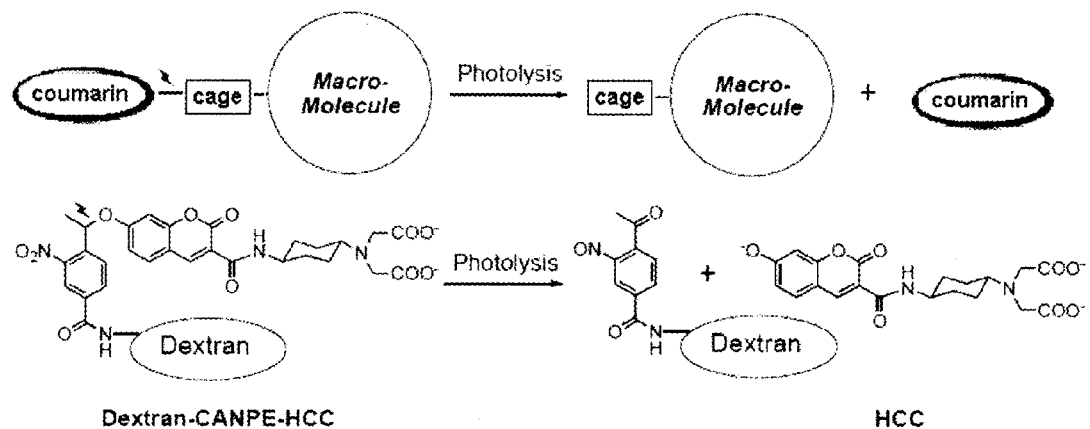

To solve the problem of cellular delivery, and to develop a more general method of using caged probes in living model organisms, a new class of bioconjugates of caged probes was designed. In this design, a macromolecule such as dextran serves as a carrier for the caged probe. Importantly, dextran is linked to a fluorophore indirectly through the caging group. Upon photolysis, such as by UV light, the fluorophore is released from the dextran carrier and becomes fluorescent and freely diffusible, and passes through gap junction channels, This design is distinct from conventional bioconjugates of caged dyes in which a fluorophore is permanently linked to a macromolecule (Mitchison, et al. 1998). The differences are illustrated in FIG. 3, in which the conventional bioconjugates are shown in FIG. 3(a) and the new bioconjugates are shown in FIG. 3(b). In FIG. 3, NPE is 1-(2-nitrophenyl)-ethyl, HCC is 7-hydroxy-coumarin 3-carboxamide, and CANPE is 1-(4-carbamoyl-2-nitrophenyl)ethyl.

The current invention also pertains to methods for using fluorescence to observe cell-cell coupling and cell-cell communication in living animals, as well as patterns of junctional cell coupling in any cells of interest, comprising the steps of injecting the animals or the cells with the type 2 bioconjugate of FIG. 3 to produce labeled animals, directing a light of certain wavelength, such as UV lights to the labeled animals at a region of interest to produce a region of fluorescence, and observing the region of fluorescence. Observing how the fluorescent dye moves throughout the cells provides valuable insight into cell-cell coupling and gap junction transfer.

Both adults and developing embryos of model organisms are suitable biological subjects for studying gap junction coupling. It has been recognized that cell-cell communication via gap junction channels plays important roles in cell specification, differentiation, and the orderly development of multicellular organisms. To gain further insights into the developmental significance of gap junction coupling, it would be desirable to construct a high resolution communication map which marks the occurrence, the strength, and the dynamics of junctional coupling with sufficient resolution over the course of development. Because of its limited cell number, C. elegans was chosen to achieve this ambitious goal. Using this new class of bioconjugates of caged fluorophore, it was possible to systematically characterized the dynamics of dye transfer from the 2-cell to the late 4-cell stage, and examined the coupling pattern near the embryo posterior from the 8-cell to the 28-cell stage. The imaging experiments revealed a very dynamic pattern of selective cell coupling during early development. Strong cell coupling was first seen between AB daughter cells at the 3-cell stage. When P1 daughter cells finished cytokinesis, they also established strong coupling, so an early 4-cell embryo has two communication compartments: one containing ABa and ABp, and the other containing EMS and P2. However, these two distinct coupling domains were only present transiently. By the late 4-cell stage, ABa, ABp, and EMS formed a strong communication compartment which was poorly connected with the P2 cell, the germline precursor. The weak communication between P2 and other somatic cells persisted during subsequent cell divisions. When the embryo developed to the 28-cell stage, all six founder cells, AB, MS, E, C, D, and P4, were born. Among them and their daughter cells, D and P4 cells appeared to be the only two cells that were separated from the somatic communication compartment.

This high resolution map of cell-cell coupling offers much more dynamic and detailed information than what was known previously about cell communication during the early embryogenesis of C. elegans. In contrast to the results herein, as discussed above, Bossinger and Schierenberg examined dye transfer in C. elegans embryos by microinjection and iontophoresis of Lucifer Yellow dye and concluded that from the 4-cell stage all blastomeres were well coupled, and that restricted dye diffusion did not start until P4 and D cells are born. The failure to identify the transient coupling domains in early developing embryos could be due to several technical limitations of microinjection, including low temporal resolution or cell damage, poor quantification of dye transfer kinetics or coupling strength, and difficulty of reliably injecting the dye into a cell at precise moments of development or cell cycle. In addition, Lucifer Yellow binds strongly to yolk granules in early C. elegans embryos. This further complicated the interpretation of dye diffusion data and diminishes the accuracy and sensitivity of measuring the rate of cell-cell dye transfer.

Furthermore, because the bioconjugates are retained in cells throughout development after being delivered into oocytes, the current invention also pertains to methods involving injecting the bioconjugates into the reproductive cells of parents for passage to embryos. The developing embryos will then also contain the bioconjugates, which can be subjected to UV light to create regions of fluorescence that can be observed and studied.

The current invention also pertains to a method for quantifying and comparing the coupling strength, or degree of interactivity, between pairs of coupled cells. To compare the relative cell coupling strength, the ratio of the initial slope of coumarin intensity increase in recipient cells after uncaging a donor cell was calculated. Since the concentration gradient between donor cells and recipient cells is the highest right after uncaging, the initial slope of dye intensity in recipient cells should be the most sensitive readout of how well cells are coupled by gap junction channels. This quantification procedure was designed to remove the effects of the initial light scattering, of the subsequent dye leakage, as well as of the indirect dye transfer from a donor to a recipient through an intermediate cell. In addition, using the ratio of the initial slopes of intensity change to assess the relative coupling efficiency among blastomeres reduced or eliminated variations in absolute fluorescence intensities from experiment to experiment, thus allowing comparing results obtained from different embryos.

EXAMPLE 1

Synthesis of Type II Dextran Conjugate (Dextran-CANPE-HCC)

Figure 4A:
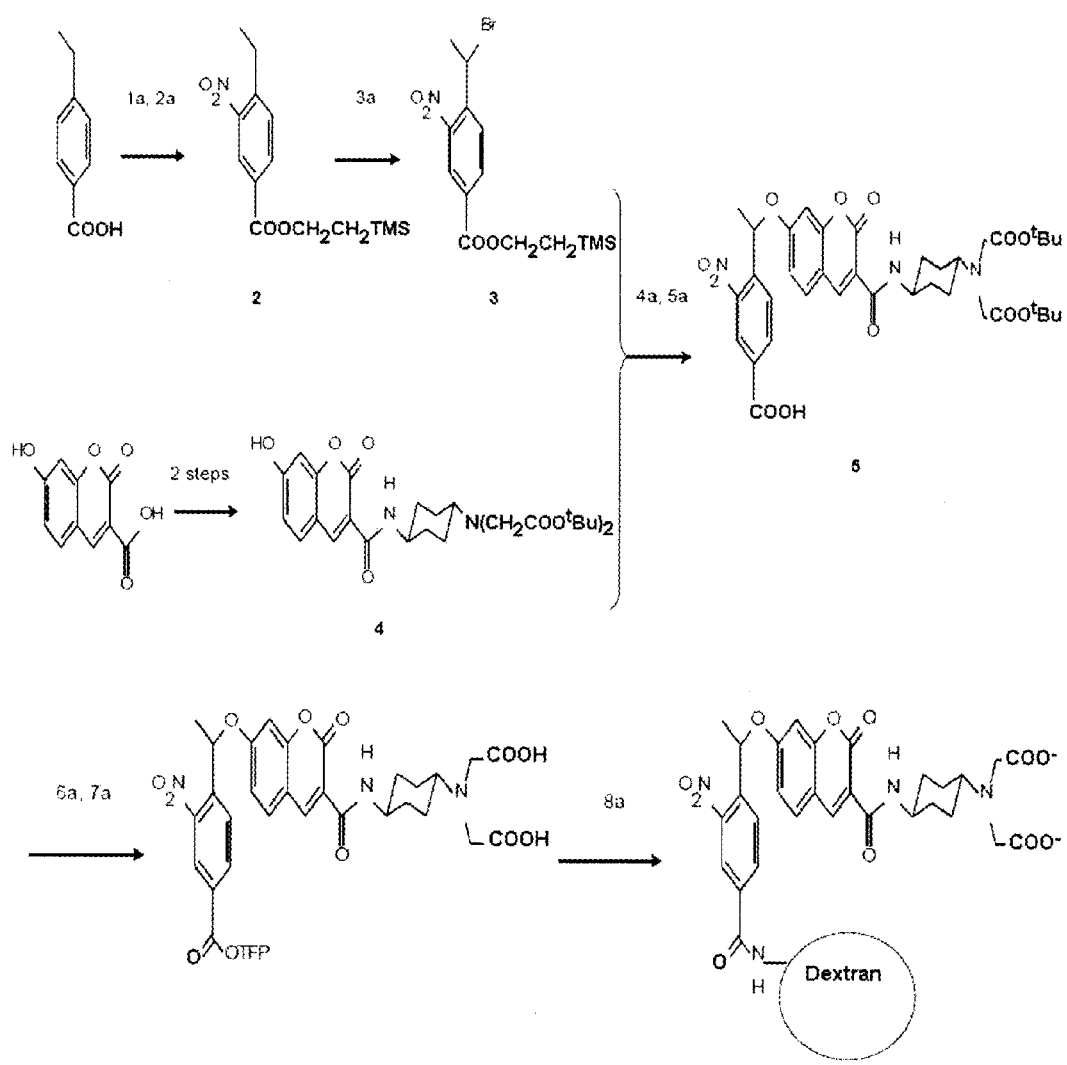
FIG. 4 shows (a) the synthesis of dextran-CANPE-HCC (b) fluorescence emission spectra of dextran-CANPE-HCC (1 μM) before and after complete photolysis (Ex=410 nm, 20 mM Mops buffer, pH 7.35). (c, d) Time course of photoconversion of dextran-CANPE-HCC (circle) and NPE-HCC (triangle, reference compound) photolyzed at 365 nm (c) or at 740 nm by two photon excitation (d)
Figure 4B:
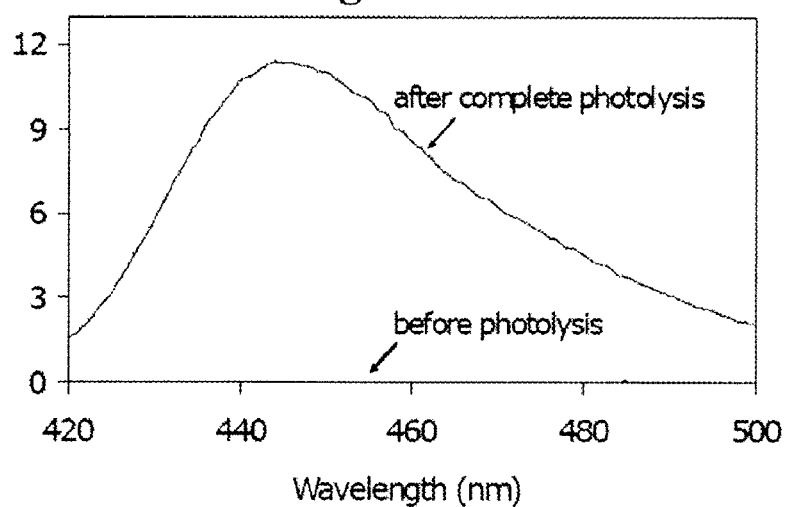
Figure 4C:
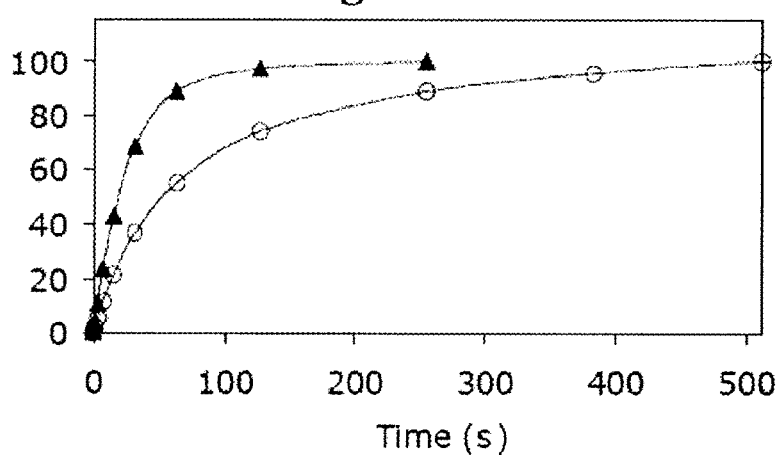
Figure 4D:
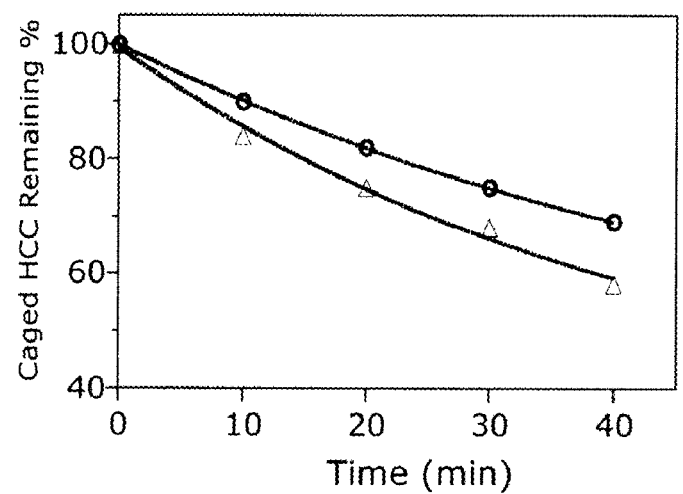

In general, to conjugate dextran with coumarin through a caging group, the NPE (1-(2-nitrophenyl)ethyl) group was modified by introducing a carboxylate at the 4-position of the phenyl ring to generate 1-(4-carboxy-2-nitrophenyl)ethyl group, as shown in FIG. 4(a). This carboxylate is then activated to form an amide bond with the amino group of dextran amines. Subsequent dialysis provides the target molecule, dextran-CANPE-HCC, in which CANPE (1-(4-carbamoyl-2-nitrophenyl)ethyl) stands for the new caging group; and HCC represents the parent coumarin fluorophore, 7-hydroxy coumarin 3-carboxamide.

FIG. 4 shows the specific steps taken to synthesize dextran-CANPE-HCC. All reagents were purchased from Aldrich or Fluka (St. Louis, Mo.). Anhydrous solvents were stored over activated molecular sieves (3 Å or 4 Å). Thin layer chromatography ("TLC") was performed on precoated silica gel 60F-254 glass plates (EM Science, Gibbstown, N.J.). Reaction products were purified by low pressure flash chromatography (FC) using silica gel 60 (63~200 μm, EM Science). $^1$H-NMR spectra were acquired on Varian 300 MHz or 400 MHz spectrometers (Varian, Palo Alto, Calif.). Chemical shifts (δ, ppm) were reported against tetramethylsilane (0 ppm). MALDI-TOF Mass Spectroscopy was performed on a Voyager-DE PRO biospectrometry workstation (Applied Biosystems, Foster City, Calif.) using 2,5-dihydroxy benzoic acid as the matrix.

With reference to FIG. 4, first, (2-trimethylsily)ethyl-4-ethyl-3-nitrobenzoate (2) was prepared, (1a) $HNO_3$, −15° C., 95%. (2a) 2-Trimethylsilylethanol, EDC.HCl, pyridine, MeCN, 67%. 4-Ethylbenzoic acid (1.5 g, 10 mmol) was slowly added to fuming nitric acid (90%, 8 mL) at −15° C. The reaction was continued at this temperature for 3 hours. The mixture was then poured into ice. The resulting precipitate was collected by filtration, washed with water, and dried under high vacuum to yield a white solid (1.86 g, 95%) which was used directly for the next step. At 0° C., N-(3-dimethylaminopropyl)-N'-ethylcarbodiimide hydrochloride (EDC.HCl, 1.77 g, 9.22 mmol), 2-(trimethylsily)ethanol (1.32 mL, 9.22 mmol) and pyridine (1.24 mL, 15.36 mmol) were successively added to an acetonitrile solution (20 mL) containing 4-ethyl-3-nitrobenzoic acid (1.50 g, 7.68 mmol). The mixture was stirred under argon at 0° C. for 3 hours and then at 25° C. for additional 15 hours. After removing the solvent under vacuum, the residue was purified by FC eluting with hexane/EtOAc (20:1 to 10:1)). The product was obtained as an oil (1.51 g, 67%). $^1$H NMR (400 MHz, δppm, $CDCl_3$): 8.51 (s, 1H), 8.17 (d, J=8.4 Hz, 1H), 7.46 (d, J=8.4 Hz, 1H), 4.45 (t, J=8.4 Hz, 2H), 2.97 (q, J=7.6 Hz, 2H), 1.30 (t, J=7.6 Hz, 3H), 1.14 (t, J=8.4 Hz, 2H), 0.09 (s, 9H).

Next, (2-Trimethylsily)ethyl-4-(1-bromo)ethyl-3-nitrobenzoate (3) was prepared, (3a) NBS, benzoyl peroxide, reflux, benzene, 83%. N-bromosuccinimide (NBS, 651 mg, 3.66 mmol) and benzoyl peroxide (30 mg) were added to a benzene solution containing (2) (720 mg, 2.44 mmol). The reaction mixture was refluxed for 14 hours and then concentrated under vacuum. The residue was purified by FC eluting with hexane/EtOAc (20:1) to give 775 mg (83%) of product as a pale yellow oil. $^1$H NMR (400 MHz, δppm, $CDCl_3$): 8.46 (s, 1H), 8.26 (d, J=8.4 Hz, 1H), 7.97 (d, J=8.4 Hz, 1H), 5.79 (q, J=6.8 Hz, 1H), 4.46 (t, J=8.8 Hz, 2H), 2.09 (d, J=6.8 Hz, 3H), 1.15 (t, J=8.8 Hz, 2H), 0.09 (s, 9H).

Next, 7-Hydroxy-coumarin 3-carboxamide (4) was prepared. This compound was prepared from 7-hydroxy-coumarin 3-carboxylate and N,N-di-tert-butylacetate 1,4-trans-diaminocyclohexane following a procedure of making a similar compound[2]. $^1$H NMR (400 MHz, δppm, $CDCl_3$): 8.81 (d, J=8.0 Hz, 1H), 8.76 (s, 1H), 7.52 (d, J=8.0 Hz, 1H), 6.9 (m, 2H), 3.85 (br, 1H), 3.42 (s, 4H), 2.7 (br, 1H), 2.09 (m, 2H), 1.94 (br, 2H), 1.42 (s, 18H), 1.2-1.4 (m, 4H). MS: 530.26 calcd for $C_{28}H_{38}N_2O_8$; obsd: 531.78 $[M+H]^+$, 553.77 $[M+Na]^+$.

Next, 7-{1-[4-(2-trimethylsilylethoxy)carbonyl-2-nitrophenyl]ethoxy}-coumarin 3-carboxamide (5a) was prepared, (4a) DIEA, $CH_3CN$, 65° C., 51%. Compounds (4) (280 mg, 0.53 mmol) and (3) (296 mg, 0.79 mmol) were mixed in $CH_3CN$ (3 mL) and diisopropylethylamine (DIEA, 183 μL, 1.1 mmol). The mixture was heated at 65° C. for overnight. After cooling, the reaction mixture was diluted with EtOAc, washed with saturated $NH_4Cl$, dried over $Na_2SO_4$, concentrated under vacuum and purified by FC eluting with hexane/EtOAc (5:1 to 3:2) to yield the product as pale yellow solid (220 mg, 51%). $^1$H NMR (400 MHz, δppm, $CDCl_3$): 8.76 (s, 1H), 8.71 (s, 1H), 8.58 (d, J=8.0 Hz, 1H), 8.24 (d, J=8.4 Hz, 1H), 7.79 (d, J=8.0 Hz, 1H), 7.53 (d, J=8.8 Hz, 1H), 6.88 (d, J=8.8 Hz, 1H), 6.65 (s, 1H), 6.17-6.21 (m, 1H), 4.44 (t, J=6.8 Hz, 2H), 3.85 (br, 1H), 3.42 (s, 4H), 2.64 (br, 1H), 2.1 (br, 2H), 1.9 (br, 2H), 1.76 (d, J=6.4 Hz, 2H), 1.4 (s, 18H), 1.2-1.43 (m, 4H), 1.15 (t, J=8.4 Hz, 2H). MS: 823.37 calcd for $C_{42}H_{57}N_3O_{12}Si$; obsd: 846.27 $[M+Na]^+$.

Next, 7-{1-[4-(2,3,5,6-tetrafluorophenoxy)carbonyl-2-nitrophenyl]ethoxy}-coumarin 3-carboxamide (TFP ester of 5) was prepared, (5a) Tetrabutylammonium fluoride, THF, 66%. Compound 5a (84 mg, 0.1 mmol) was dissolved in 0.8 mL THF. Tetrabutyl-ammonium fluoride (0.2 mL, 1M in THF) was added in one portion. The reaction was followed by TLC until it reached completion. After removing solvent under vacuum, the mixture was passed through a short silica gel column and used directly for the next step.

Next, the above free acid (compound (5), 48 mg, 66 μmmol) was dissolved in $CH_2Cl_2$ (1 mL). 2,3,4,5-Tetrafluorophenol (22 mg) and EDC.HCl (25 mg) were added. (6a) Tetrafluorophenol (TFP), EDC.HCl, DMAP, 89%. (7a) TFA, $CH_2Cl_2$. The reaction was continued overnight and purified by FC eluting with ethyl acetate/hexane (1:2 to 1:1). A total of 51 mg (59% for 2 steps) of product was obtained. $^1$H NMR (400 MHz, δppm, $CDCl_3$): 8.88 (d, J=1.6 Hz, 1H), 8.76 (S, 1H), 8.53 (d, J=8.0 Hz, 1H), 8.40 (dd, J=8.0, 1.6 Hz, 1H), 7.91 (d, J=8.0 Hz, 1H), 7.55 (d, J=8.8 Hz, 1H), 7.02-7.12 (m, 1H), 6.90 (dd, J=10, 2.4 Hz, 1H), 6.73 (d, J=2.4 Hz, 1H), 6.22-6.27 (m, 1H), 3.84 (br, 1H), 3.45 (s, 4H), 2.70 (br, 1H), 2.0-2.1 (m, 2H), 1.9-2.0 (m, 2H), 1.78 (d, J=6.4 Hz, 3H), 1.44 (s, 18H), 1.28-1.40 (m, 4H). MS: 871.29 calcd for $C_{43}H_{45}F_4N_3O_{12}$; obsd: 872.62 [M+H]$^+$, 894.59 [M+Na]$^+$, 910.55 [M+K]$^+$.

Finally, dextran-CANPE-HCC was prepared, (8a) Dextran amine (40 KD), triethylamine, DMSO, then dialysis. The above TFP ester of compound (5) (4.2 mg) was dissolved in $CH_2Cl_2$/TFA (1:1, 0.1 mL). The reaction was monitored by TLC until the deprotection went to completion to generate compound (6). The removal of both tert-butyl groups was confirmed by Mass Spectroscopy analysis. MS: 759.17 calcd for $C_{35}H_{29}N_3O_{12}F_4$; obsd: 760.59 [M+H]$^+$, 782.57 [M+Na]$^+$. The dried product dissolved in DMSO to make a 10 mM stock solution. Dextran amines (40 KD, ~8 amines/dextran) was dissolved in DMSO to a final concentration of ~4.2 mM dextran. It was then mixed with the above stock solution containing TFP ester of caged coumarin 3-carboxamide at a volume ratio of 1:4. An excess of triethylamine was added as the proton scavenger. The reaction was continued overnight at 37° C. The mixture was then dialyzed twice against Hepes buffer (20 mM, pH 7.3) and water through a cellulose membrane (Float A Lyzer™, MWCO=3,500, Spectrum Laboratories, Inc.). The dialyzed product was freeze dried and dissolved in water to make a stock solution of 10 mM, quantified by the absorption of caged coumarin.

EXAMPLE 2

Synthesis of Type I Dextran Conjugate (Dextran-HCC-NPE) of Caged Coumarin

Excess acetic anhydride (~4 μL) was added to a solution of NPE-HCC (2 mg, 3.5 μmol, prepared similarly as described (Zhao et al., 2004) in pyridine (70 μL). The mixture was stirred at 65° C. for 6 h and dried under vacuum. The resulting anhydride was dissolved in a small amount of benzene and dried again to remove the residual acetic anhydride.

The above cyclic anhydride was dissolved in DMSO to a concentration of 8 mM. Dextran amines (Molecular Probes, 10 KD, ~2.6 amines/dextran) in DMSO (100 mg/mL) was then mixed with the cyclic anhydride solution in DMSO at a molar ration of 1:1.2 (amines:anhydride). Two equivalents of DIEA was added as the proton scavenger. The resulting mixture was incubated at 37° C. overnight and then diluted with MOPS buffer (pH 7.3). The mixture was dialyzed against MOPS buffer (pH 7.3) and water, lyophilized to yield the product as a white powder.

EXAMPLE 3

Caged Coumarin Comparative Example

To study cell junctional coupling in living worms, a caged and cell permeable coumarin dye, NPE-HCCC2/AM (Dakin et al., 2005 and Zhao, et al., 2004), was initially used to load cells. NPE-HCCC/AM (2 mM in DMSO, 1 μL), was mixed with Pluronic® F127 (BASF, Ludwigshafen, Germany) (10% in DMSO, 1 μL) in 50 μL of *E. Coli* HB101 liquid culture. The mixture was then placed on the top of a thin layer of 2% agar pad. A small number of N2 larvae or young adults were then transferred to the agar pad. After overnight incubation in a wet chamber, worms were photolyzed by UV light (360±20 nm) and imaged on a Axiovert 200 microscope. After illuminating worms with UV light on a microscope, there was no fluorescence intensity increase detected above the background level, possibly because the worm cuticle is a barrier to efficient dye uptake. Feeding worms with the caged dye by premixing it with bacteria helps the dye enter worms only in low efficiency, and the loaded dye is restricted to intestinal lumen or cells lining the gut. Overall, the cellular loading was highly inefficient.

EXAMPLE 4

Fluorescence, Photolytic Efficiency, and Uncaging

FIG. 4(*b*) shows the fluorescence emission spectra of dextran-CANPE-HCC (1 μM) before and after complete photolysis (Ex=410 nm, 20 mM Mops buffer, pH 7.35). FIG. 4(*c,d*) shows the time course of photoconversion of dextran-CANPE-HCC (circle) and NPE-HCC (triangle, reference compound) photolyzed at 365 nm (c) or at 740 nm by two photon excitation (d). It took longer time for the two photon uncaging to be detected to an appreciable degree because the accumulated photolysis of the bulk solution was being measured, whereas two photon excitation only occurs at the focal point of a laser beam.

Dextran-CANPE-HCC has negligible fluorescence. After complete photolysis at 365 nm, the fluorescence intensity of the sample increases over 260-fold with 410 nm excitation, as shown in FIG. 4(*b*). This large fluorescence increase ensures a robust contrast enhancement after uncaging. Measurements of the quantum efficiency of photolyzing dextran-CANPE-HCC by UV or two photon excitation were performed using the same procedures as previously described (Zhao, et al., 2004). NPE-HCC, a compound with a known UV uncaging quantum yield of 53% at 365 nm and a two photon uncaging cross section of 0.68 GM at 740 nm (Zhao, et al., 2004), was used as a reference. Briefly, the one photon photolysis quantum yield was determined by irradiating about 1 μM of dextran-CANPE-HCC in a buffer containing 10 mM Kmops and 100 mM KCl (pH 7.3). UV light (365 nm) from a mercury lamp (B-100 AP, UVP, Upland, Calif.) was controlled by an electronic shutter (Uniblitz, Vincent Associates, Rochester, N.Y.) to gate the exposure time. After each episode of UV exposure, fluorescence emission spectra of the sample were recorded on a Fluorolog 3 spectrometer (Jobin-Yvon Horiba, Edison, N.J.). The UV uncaging quantum yield of dextran-CANPE-HCC was calculated by comparing its initial rate of photolysis at 365 nm with that of NPE-HCC.

Two photo photolysis was carried out in a microcuvette (45 μL, Hellma 105.251-QS) containing 10 μM of caged dye in 100 mM Mops buffer (pH 7.3). The laser beam from a femtosecond-pulsed and mode-locked Ti:sapphire laser (Coherent, Santa Clara, Calif.) was focused into the center of the cuvette with a focusing lens (01 LPX 029/077, focal length 25 mm, Melles-Griot, Carlsbad, Calif.). After irradiation with 740 nm light (345 mW laser power exiting the cuvette), samples were collected and diluted to 1 μM with Mops buffer. The formation of the product was quantified by measuring fluorescence enhancement. The two photon uncaging cross section of dextran-CANPE-HCC was calculated by comparing its initial rate of photolysis at 740 nm with that of NPE-HCC.

The uncaging efficiency of NPF-caged coumarins is extraordinarily high, about two orders of magnitude higher than caged fluorescein or rhodamine (Dakin et al., 2006 and Zhao et al., 2004). This major improvement makes it possible to use much lower doses of UV light to photo-activate, thus minimizing photodamage. This is an important consideration for live cell imaging, especially in experiments involving developing embryos that are more sensitive to phototoxicity (Squirrell et al., 1999). Dextran-CANPE-HCC retains high photolytic efficiency, close to that of NPE-caged coumarin, as shown in FIGS. 4(*c*) and 4(*d*). Its UV uncaging cross section (product of the uncaging quantum yield ($Q_u$) and extinction coefficient (ε) at 365 nm) was calculated to be 5,000 $M^{-1}$ $cm^{-1}$, and its two photon uncaging cross section was calculated to be 0.5 Goeppert-Mayer (GM, 1 GM=$10^{-50}$ $cm^4 \cdot s$/photon) at 740 nm. Both values are sufficiently high for live cell imaging applications.

EXAMPLE 5

Cell Coupling in Early Developing Embryos

To introduce dextran-CANPE-HCC into *C. elegans*, the probe was injected into the distal end of gonads of young hermaphrodites. *C. elegans* strains, including wild type Bristol N2 and RW10006 (Bao et al., 2006) were maintained as described (Brenner 1974). To label oocytes and embryos, dextran-CANPE-HCC (3-4.5 mM of caged HCC measured by its absorbance at 350 nm, using $\epsilon^{350\,nm}$=22,000 $M^{-1}$ $cm^{-1}$) and dextran-rhodamine (40 KD, Sigma, 4-5 mg/mL) were injected. Rhodamine-dextran was coinjected as a fluorescent marker. The injected dye was observed to gradually fill the syncytium of gonad and could be detected in fertilized embryos in a few hours. These labeled embryos developed normally into adults, and they behaved the same as control unlabeled worms, suggesting that neither rhodamine-dextran nor dextran-CANPE-HCC affects embryonic development or the behavior of adult worms. Moreover, throughout the development, labeled embryos showed little coumarin fluorescence signal, yet they displayed robust coumarin fluorescence after uncaging, confirming that dextran-CANPE-HCC is chemically and metabolically stable in vivo.

Without wanting to be bound by theory, the development of *C. elegans* has proved to be invariant. The fertilized egg first cleaves into a larger anterior cell, the AB cell, and a smaller posterior cell, the P1 cell. Division of the AB cell generates ABa and ABp, and division of the P1 cell produces EMS and P2 cells. Subsequent divisions give rise to the MS and E cells (daughters of EMS), and C and P3 cells (daughters of P2). Later, when the P3 cell divides, it generates D and P4 cells at the 28-cell stage. By this time, all six founder cells, AB, MS, E, C, D, and P4 are generated. P4 is the precursor of germ cells, while other founder cells develop into somatic cells.

To study the pattern of cell-cell coupling during early development, embryos were collected from injected worms and subjected to differential interference contrast ("DIC") imaging. Three to four hours after injection, early embryos were collected from injected worms by cutting the worms near the uterus. Labeled embryos were transferred onto a 2% agar pad, covered with a coverslip, and mounted on an inverted fluorescence microscope (Axiovert 200M, Carl Zeiss, Peabody, Mass.). During uncaging and imaging, motorized filter wheels (Ludl Electronics Products, Hawthorne, N.Y.) were employed to select excitation and emission wavelengths by passing light from a Xeon lamp (75 W) through bandpass filters (Chroma Technology, Rockingham, Vt.). A neutral density filter was also added to the light path to reduce the excitation light intensity by about 70%. The typical UV uncaging duration is about 2 seconds. Bandpass filters were chosen for UV uncaging (360±20 nm), coumarin imaging (excitation 425±5 nm, emission 460±15 nm), GFP imaging (excitation 488±7.5 nm, emission 530±20 nm), and rhodamine imaging (excitation 560±20 nm, emission 615±30 nm). A customized multiple path dichroic mirror was used for the UV uncaging and 3-color imaging. Epifluorescence was collected with a cooled CCD camera (ORCA-ER, Hamamatsu, Bridgewater, N.J.) under the control of Open-Lab software (Improvision, Waltham, Mass.). The coupling patterns at different stages of early developing embryos are representative of at least 5 uncaging experiments.

Figure 5:
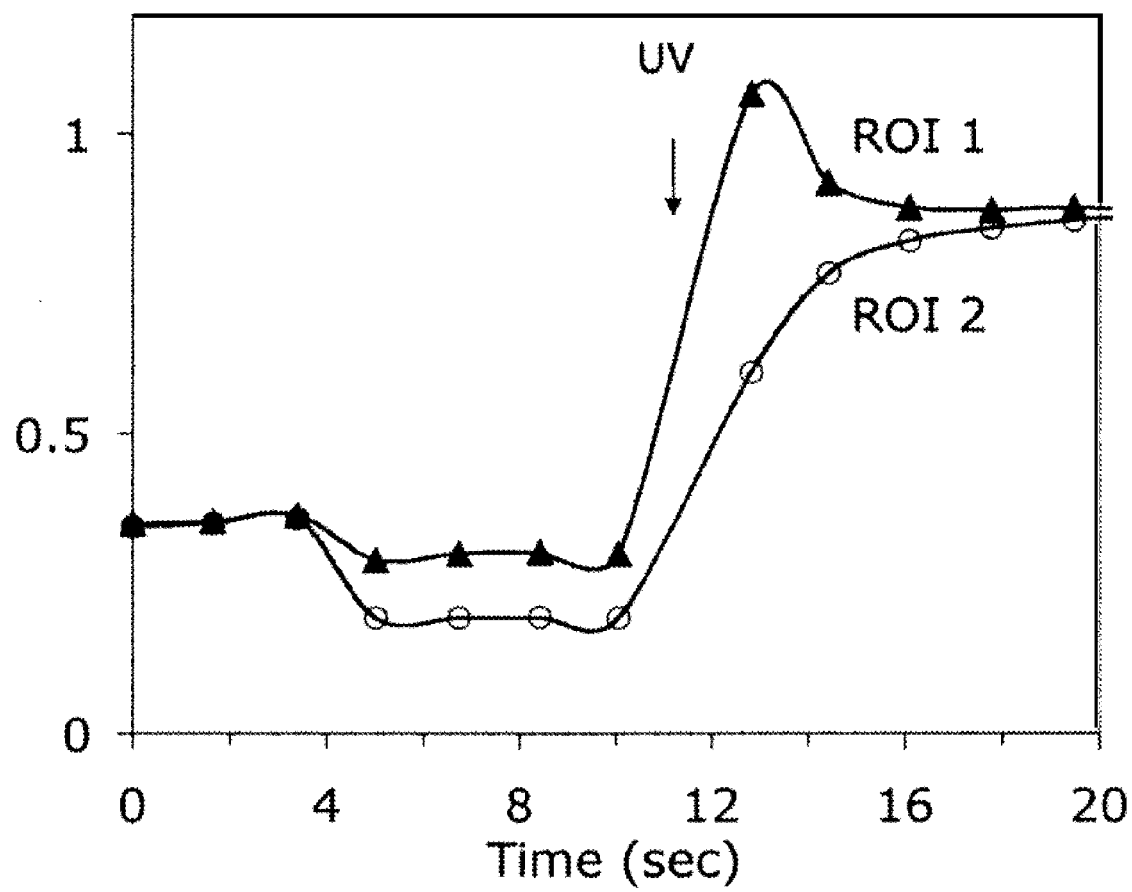
FIG. 5 shows the time course of the average HCC fluorescence intensity in two regions of interest in the embryo (ROI1 and ROI2) after local uncaging, demonstrating that HCC diffuses rapidly inside cells.

In 1-cell embryos, local uncaging at one end of an embryo generated a sudden increase in coumarin fluorescence near the uncaging area. FIG. 5 shows the time course of the average HCC fluorescence intensity in two regions of interest in the embryo (ROI1 and ROI2). Coumarin fluorescence intensity dropped between 4 sec and 10 sec when the iris of field diaphragm was reduced to allow local uncaging. The released HCC rapidly diffused across the entire cell and became equilibrated in the cytosol in approximately 6 seconds, suggesting that HCC fluorophore does not bind strongly to cytoplasmic proteins or granules, so it can diffuse quickly in the cytosol. This is an important requirement of using fluorescent tracers to track cell-cell communication, so that the rate limiting step of cell-cell dye diffusion is through gap junction channels.

Figure 6:
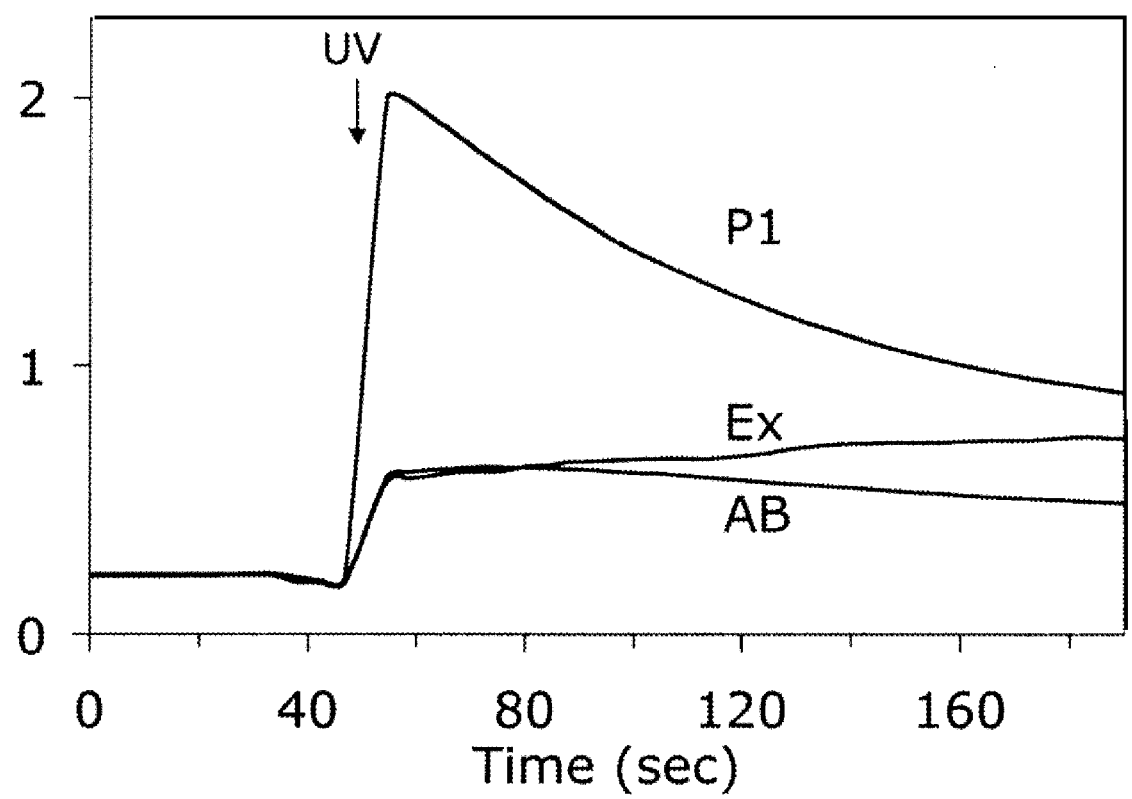
FIG. 6 shows the time course of the average HCC fluorescence in three regions of interest ("ROI") representing the bulk cytoplasm of cells P1 and AB, and an extracellular area ("Ex") within the eggshell.

When embryos developed to the 2-cell stage, dextran-CANPE-HCC was locally photolyzed in a cell. During local uncaging, a narrow beam of UV light was directed to one cell (the donor cell), targeting areas that were away from the cell-cell interface to minimize UV exposure of neighboring cells. After local uncaging, an immediate jump of coumarin fluorescence intensity was detected in neighboring cells FIG. 6 shows the time course of the average HCC fluorescence in three regions of interest ("ROI") representing the bulk cytoplasm of cells P1 and AB, and an extracellular area ("Ex") within the eggshell. Both the gradual increase in fluorescence intensity in the "Ex" ROI and the decay of P1 fluorescence suggest slow dye leakage into the extracellular space. This phenomenon was also observed in embryos at other developmental stages, and it was mainly caused by scattering of coumarin fluorescence from the donor cell to the neighboring areas. This "light bulb" effect was noticed in cultured cells at high cell confluence, but it is more pronounced in developing *C. elegans* embryos, most likely because of the extensive cell-cell contact in three dimensions, and because of the increased light scattering from yolk granules.

In the majority of experiments done in the 2-cell stage, obvious dye transfer was not detected between AB and P1 cells. Occasionally, however, there was a weak coupling between these two cells in late 2-cell embryos. In addition, a gradual leakage of HCC out of cells into the extracellular space was seen. Without wanting to be bound by theory, it possible that hemichannels or non-specific anion transporters may be responsible for this process.

Figure 7:
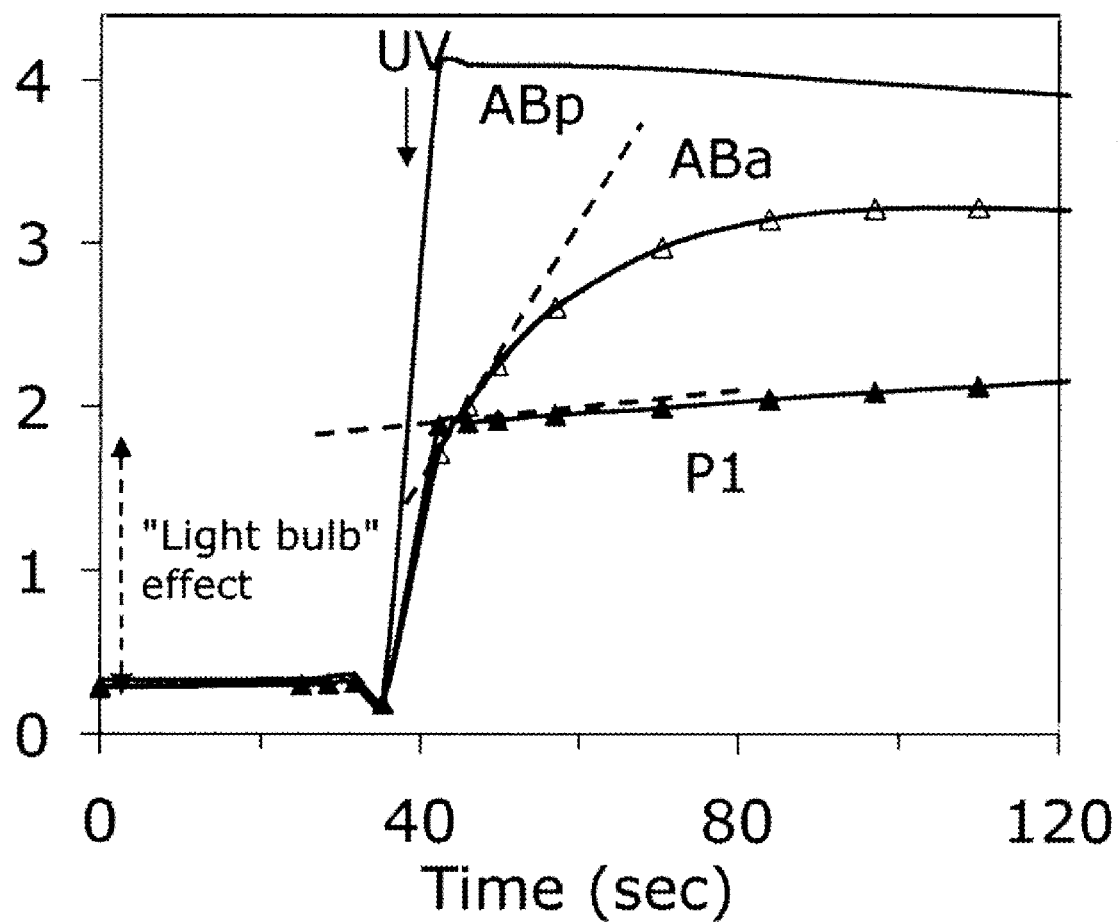
FIG. 7 shows the time course of the average HCC intensity of the bulk cytoplasm for dye transfer in 3-cell embryos.
Figure 8A:
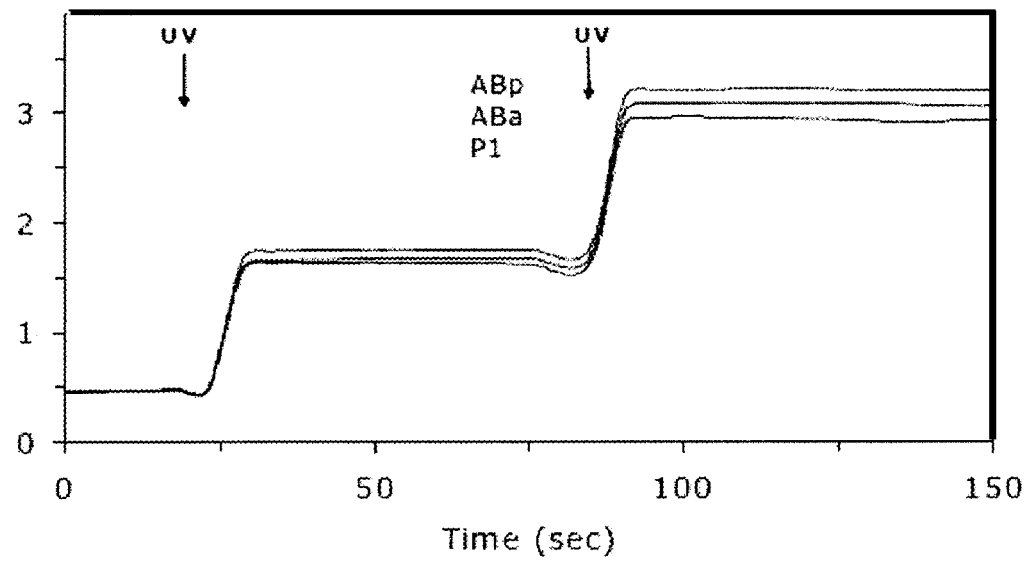
FIG. 8 shows the quantification of dextran-HCC epifluorescence in the bulk cytoplasm of early embryos after global uncaging of dextran-HCC-NPE; (a, c) Representative time courses of dextran-HCC epifluorescence of the bulk cytoplasm of a 3-cell (a) or a 4-cell embryo (c); (b, d) Quantification of the relative epifluorescence intensity of individual blastomeres.
Figure 8B:
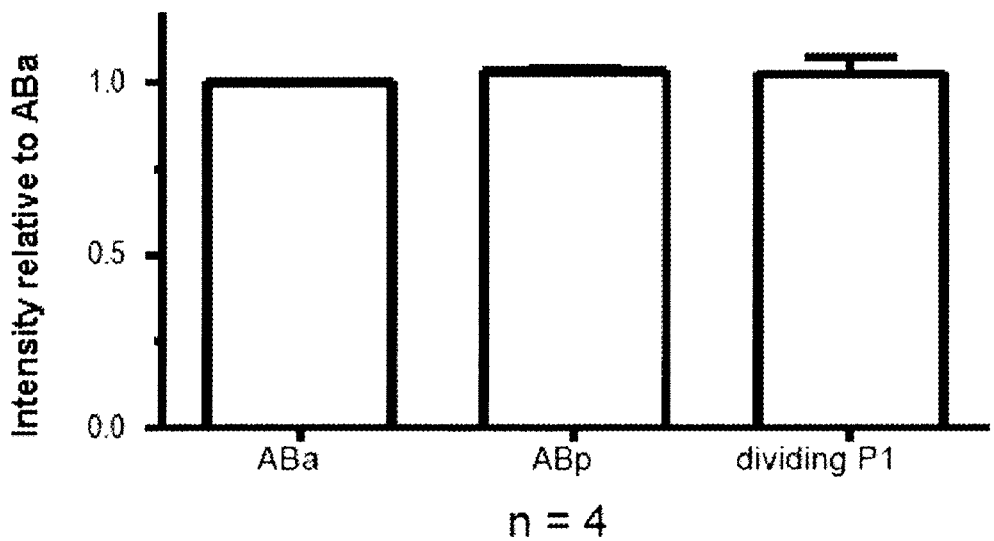
Figure 8C:
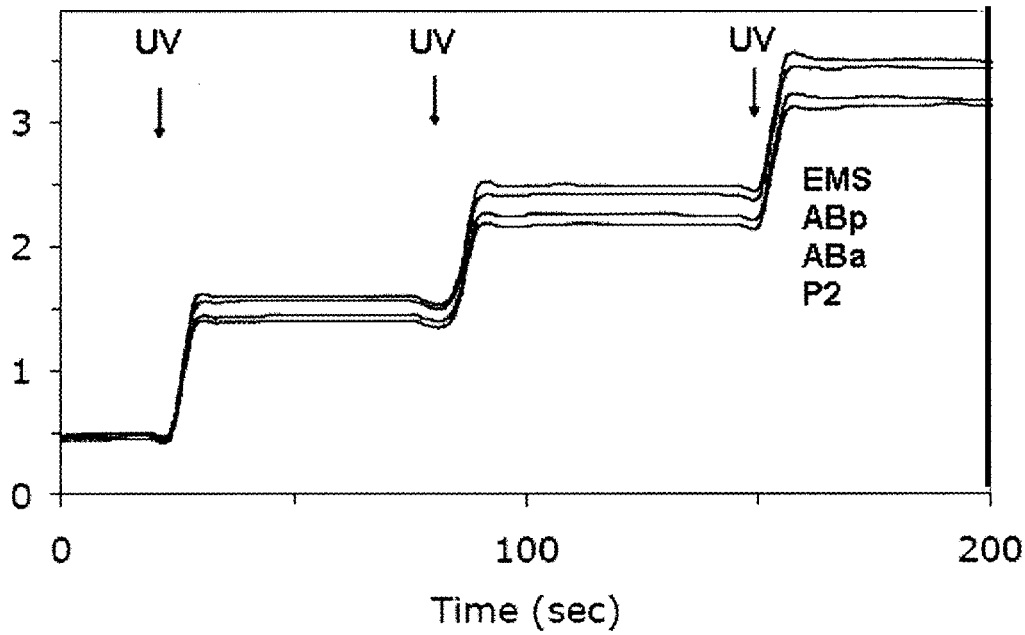
Figure 8D:
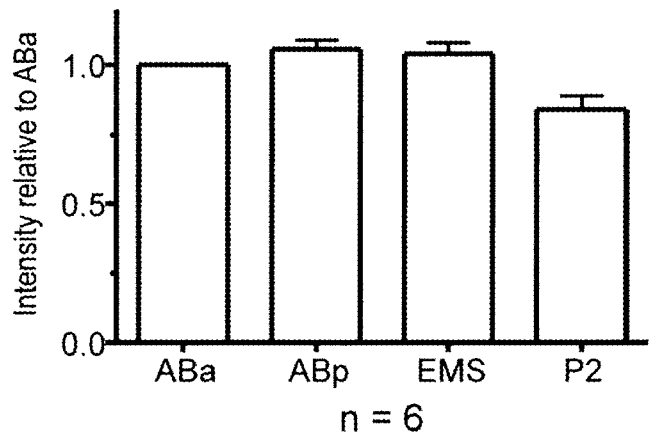

The next round of cell division starts from the AB cell, followed by the P1 cell. To define the stage of cell cycle more reliably, chromosome structure was monitored by fluorescence imaging using histone tagged GFP as the marker (pie-1::H2B::GFP, strain RW10006 (Bao et al., 2006)). When the AB cell finishes mitosis, the division of P1 was approaching telophase. When the cytokinesis of AB cells was complete (judged by the reformation of nuclear envelope in its daughter cells, by the smooth and even distribution of H2B::GFP signal, and by the appearance of a new cell-cell interface between ABa and ABp), at least another 30 seconds was allowed to pass before uncaging of one of its daughter cells, ABp. Subsequent imaging revealed that ABa and ABp were strongly coupled, and that dye transfer reached equilibrium within approximately 60 seconds. However, dye transfer between ABs and the dividing P1 cell was much slower. FIG. 7 shows the time course of the average HCC intensity of the bulk cytoplasm. The ratio between these two slopes corresponds to the relative coupling strength between the ABp/ABa pair and the ABp/P1 pair. The pattern of cell coupling is representative of six embryos assayed in the 3-cell stage. To compare the relative coupling strength between blastomeres in the 3-cell or late 4-cell embryos, the initial slope (within the first 9 sec after a local uncaging) of coumarin intensity increase was measured in the recipient cells. The coumarin intensity jump in recipient cells immediately after uncaging was mostly due to the "light bulb" effect, so it was not included when calculating the slope of the initial intensity increase. Using the ratio of the initial slope of coumarin intensity increase in recipient cells, it was quantified that the coupling between AB cells is 10.2±3.5 times (n=6) stronger than the coupling between ABp and P1 in 3-cell embryos. Even after taking into account the cell volume difference between ABp and P1, this data still suggests that AB cells are selectively coupled at much greater strength. The coupling between ABa and P1 was also very weak compared with that between AB cells (data not shown).

The relative cell coupling strength was quantified by calculating the ratio of the slopes of intensity increase in different recipient cells. To examine the correlation between the measured epifluorescence intensity with the cellular dye concentration in different blastomeres, dextran-HCC-NPE (10 KD, type 1 bioconjugate) was globally uncaged in early embryos. The fluorescence intensity of the bulk cytoplasm in all blastomeres rose to about the same level after a global uncaging (FIG. 8), confirming that the measured bulk epifluorescence intensity of different blastomeres changes similarly with respect to the dye concentration. FIG. 8 shows the quantification of dextran-HCC epifluorescence in the bulk cytoplasm of early embryos after global uncaging of dextran-HCC-NPE. UV pulses were delivered to the entire embryos as indicated by the arrows. The intensity of dextran-HCC in ABa is arbitrarily set to 1.

Figure 9:
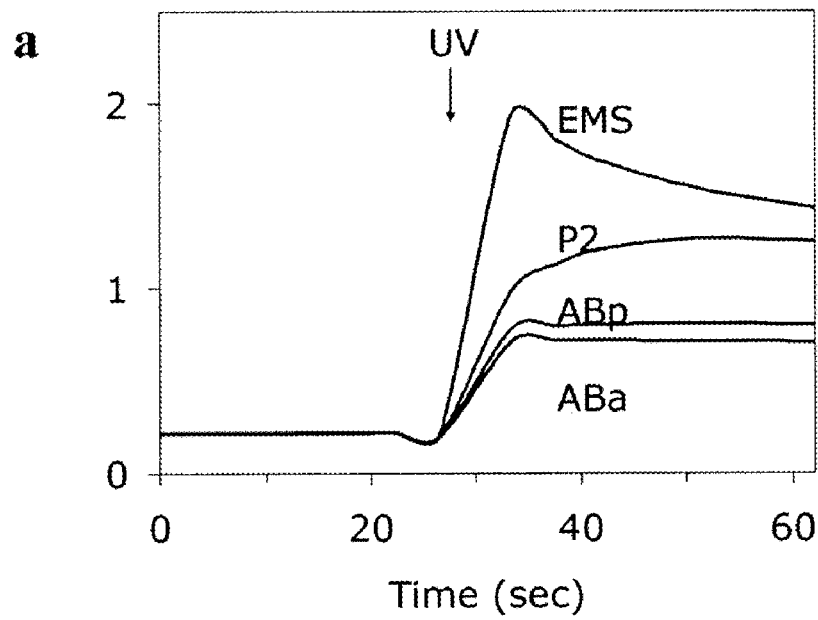
FIG. 9 shows the time course of the average HCC fluorescence intensity of the bulk cytoplasm for dye transfer in early 4-cell embryos after local uncaging of EMS (a) or ABp (b)
Figure 9:
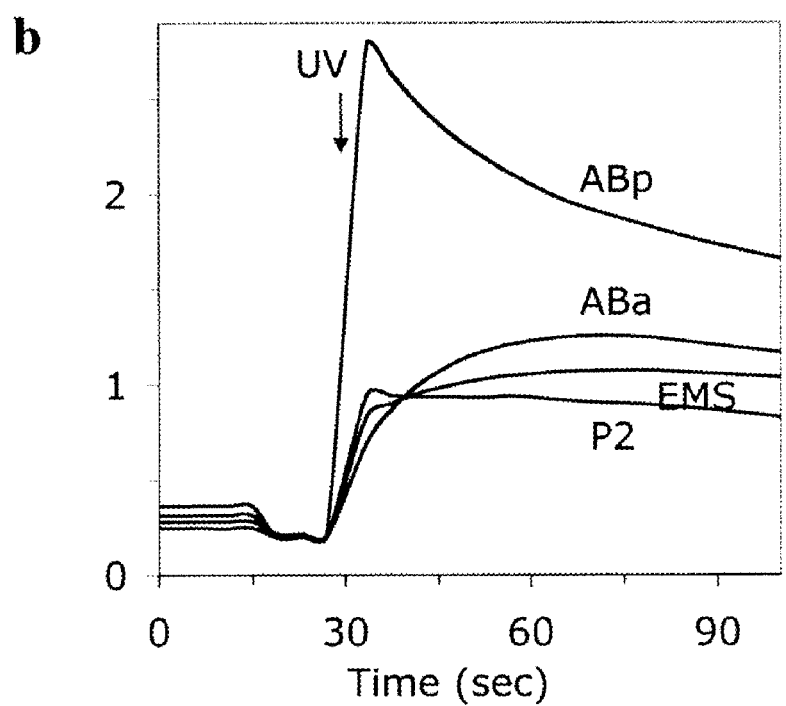

This selective coupling between AB cells persists at the early 4-cell stage. Shortly after the cytokinesis of P1 (nuclei of its daughter cells, EMS and P2, are still fairly close to the newly formed cell-cell interface), one of its daughter cells, EMS was uncaged. Coupling between EMS and P2 is strong, and there was little dye transfer to either ABa or Abp (FIG. 9(a)). Similarly, uncaging ABp showed faster dye transfer to ABa (FIG. 9(b)). FIGS. 9(a) and 9(b) show the time course of the average HCC fluorescence intensity of the bulk cytoplasm. The pattern of cell coupling is representative of five embryos assayed in the early 4-cell stage. Thus, the communication between AB or P1 daughter cells is specific and restricted at the early 4-cell stage.

Interestingly, as development progressed, the pattern of gap junction coupling among these 4-cells underwent a dynamic reorganization. Towards the mid 4-cell stage, the coupling between ABs was still strong, and there was little dye transfer from ABp to P2. At the same time, EMS started to establish communication with ABp: uncaging ABp showed obvious dye transfer from ABp to EMS; and uncaging EMS further revealed that EMS was coupled to the other three cells with roughly the same strength. By comparison with early 4-cell embryos, the coupling strength between EMS and P2 appeared to attenuate at the mid 4-cell stage.

Figure 10:
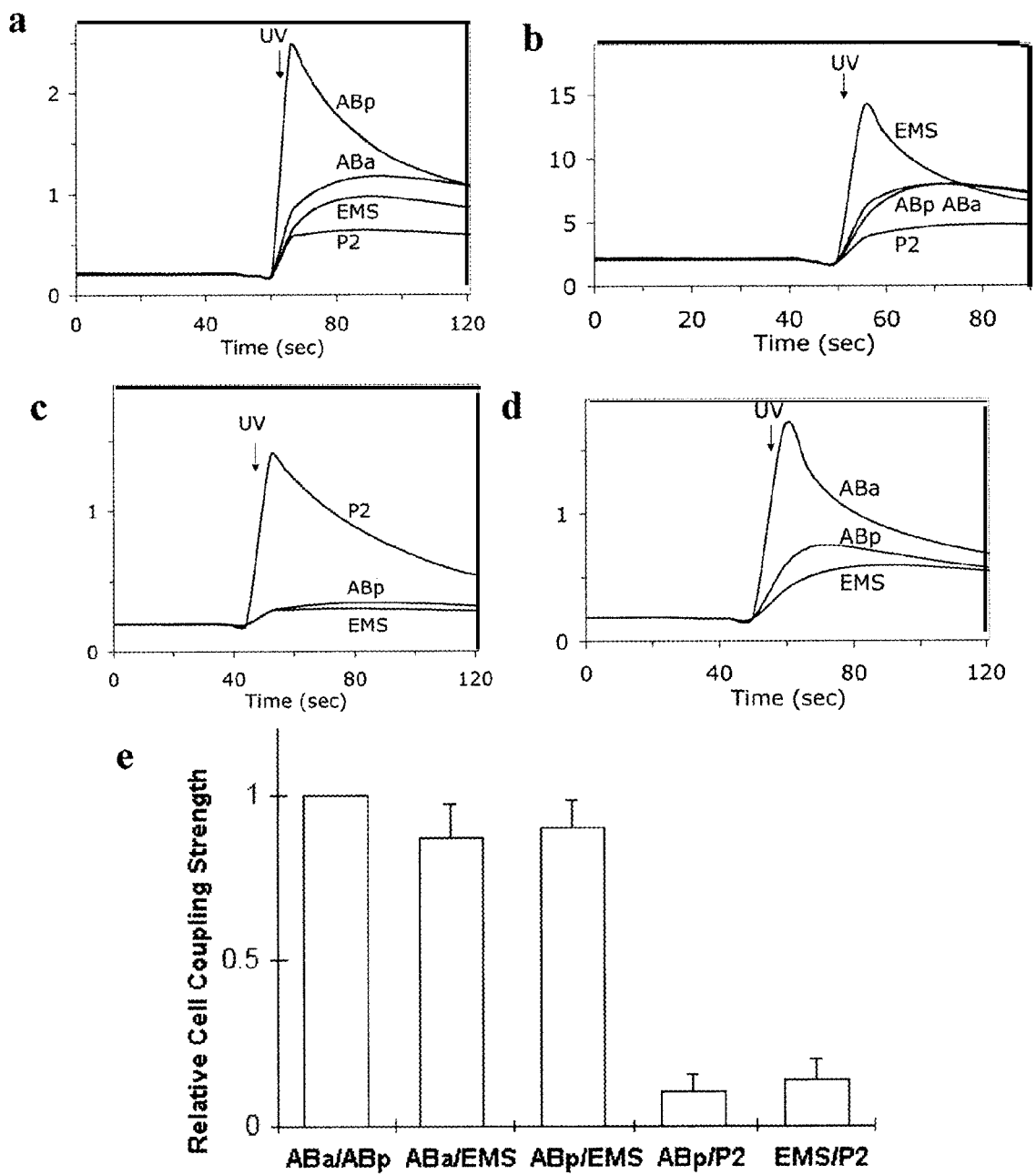
FIG. 10 shows the time course of the average HCC fluorescence intensity of the bulk cytoplasm for dye transfer in late 4-cell embryos after local uncaging of ABp (a), EMS (b), P2 (c), or ABa (d); and (e) shows the normalized relative coupling strengths (n=5) between neighboring cells calculated from the initial dye transfer data after uncaging ABp or EMS.

The coupling between P2 and EMS continued to weaken as embryos developed. By the late 4-cell stage (characterized by the elongation of EMS which projected cellular processes around ABa), P2 was nearly uncoupled from both EMS and ABp. Uncaging either ABp or EMS (FIGS. 10(a) and 10(b)) showed very slow dye transfer to P2, while the communications between ABp/EMS, ABp/ABa, and EMS/ABa were still strong. Consistent with these data, photolyzing caged coumarin in P2 showed little dye transfer to ABp or EMS (FIG. 10(c)), while uncaging ABa revealed the reciprocal strong coupling between AB cells and between ABa and EMS (FIG. 10(d)). FIGS. 10(a)-10(d) show the time course of the average HCC fluorescence intensity of the bulk cytoplasm. At the late 4-cell stage, the relative coupling strengths among these cells were quantified based on the initial slope of coumarin intensity increase in recipient cells (FIG. 10(e)). FIG. 10(e) shows the normalized relative coupling strengths (n=5) between neighboring cells calculated from the initial dye transfer data after uncaging ABp or EMS. The relative coupling strength between ABs was arbitrarily set to 1.

Similar to its parent, one of the daughter cells of the P2 cell also exhibits limited coupling with other cells. When the P2 cell divides, it generates the C and P3 cells. Like P2, these cells are located at the posterior end of developing embryos and can be identified by both DIC and fluorescence imaging. A few minutes after P3 and C were born, dextran-CANPE-HCC was uncaged at the anterior end of an 8-cell embryo. HCC dye diffused rapidly across the embryo. However, when it reached the P3 cell (interphase), dye diffusion into the P3 cell became restricted. Similar limited dye diffusion into P3 was also observed when the cell was undergoing mitosis, suggesting that the P3 cell was weakly coupled to neighboring somatic cells throughout its life. Interestingly, dye transfer to the C cell, the sister cell of P3, appeared to be the same as other somatic cells. The division of P3 generated 2 cells, P4 and D, at the posterior end in a 28-cell stage embryo. Photolysis of dextran-CANPE-HCC at the anterior end released HCC dye which rapidly diffused across the embryo. However, when HCC reached P4 and D cells, dye diffusion into these two cells nearly stopped.

EXAMPLE 6

Control Experiments

To confirm that the observed cell-cell dye transfer is through gap junction channels rather than by other mechanisms such as cytoplasmic bridges (which allow macromolecules over tens of KD to pass), control experiments were carried out by adding 18α-glycyrrhetinic acid (α-GA), a compound that has been used to block gap junction transmission (Rozental et al., 2001), to embryos when assaying cell-cell dye transfer. To deliver α-GA to blastomeres more efficiently, eggshells were thinned by treating embryos briefly by limited enzymatic digestion with bleach and chitinase. Worms injected with dextran-CANPE-HCC 3-4 hours earlier were cut upon near the uterus to release early embryos into a diluted bleach solution (sodium hypochlorite, Fisher Scientific, cat #SS290-1, diluted 10× with water). Three minutes later, the bleach solution was removed and the embryos were washed twice with water using a mouse pipette. After removing water, 10 μL of an egg salt solution (118 mM NaCl and 48 mM KCl) containing chitinase (Sigma cat #C7809-5UN, 2.5 units/mL), chymotrypsin (Sigma cat #C4129, 5 mg/mL) and α-GA (25 μM) was added to the embryos. Seven minutes later, the treated embryos were transferred to an agar pad to start uncaging and imaging. Embryos treated with bleach and enzymes but without α-GA showed normal dye transfer pattern as untreated embryos.

Figure 11:
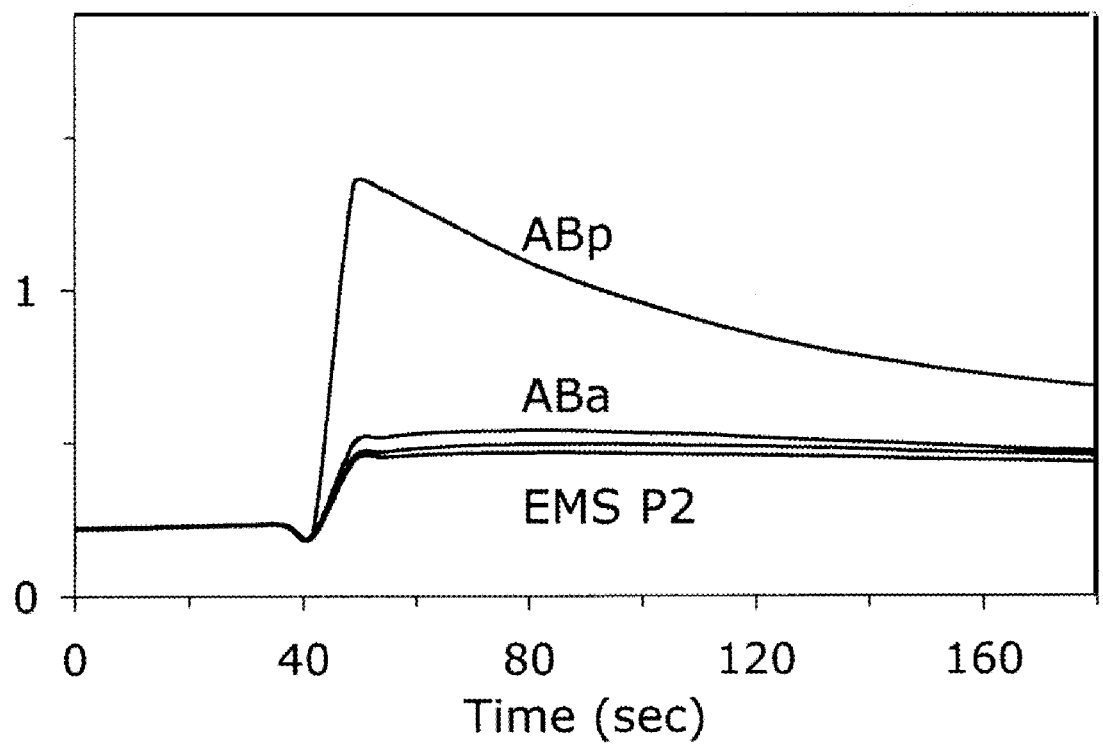
FIG. 11 shows the time course of the average HCC fluorescence intensity after uncaging dextran-CANPE-HCC in Abp. A blocker of gap junction transmission, 18-glycyrrhetinic acid (–GA) was added to an embryo whose eggshell was thinned by limited chitinase digestion.

After uncaging dextran-CANPE-HCC in a cell that was normally coupled to neighboring blastomeres, dye transfer was not observed in the presence of α-GA (FIG. 11). FIG. 11 shows the time course of the average HCC fluorescence intensity after uncaging dextran-CANPE-HCC (type II) in ABp of a 4-cell embryo that has been treated with bleach, chitinase and -GA.

Figure 12A:
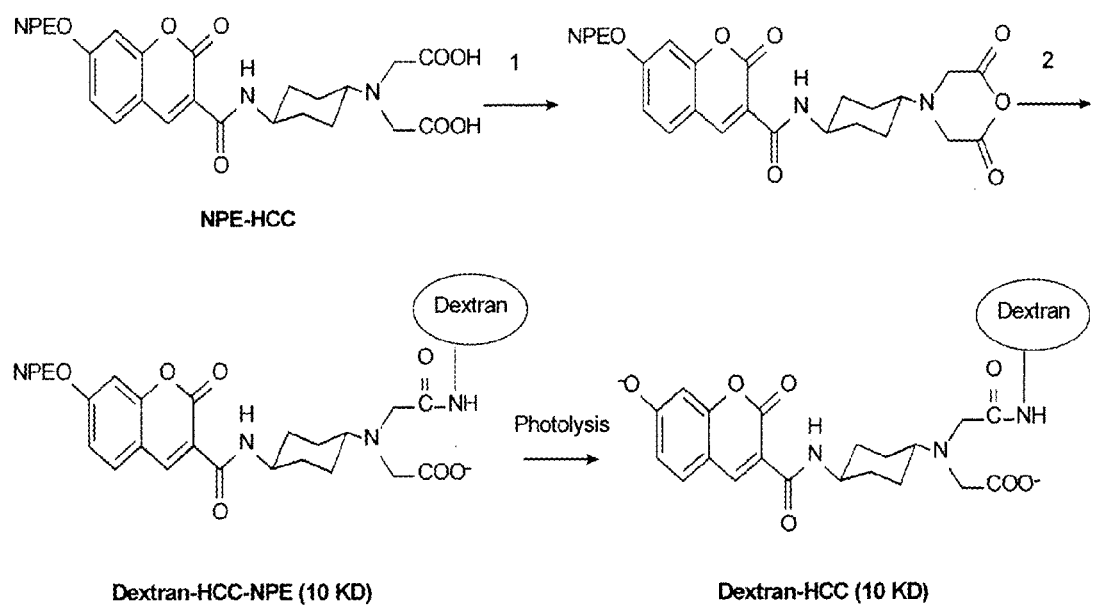
FIG. 12 shows (a) the synthesis of a type I caged coumarin-dextran conjugate, dextran-HCC-NPE, and (b) the time course of average dextran-HCC fluorescence intensity of the bulk cytoplasm after uncaging dextran-HCC-NPE in Abp cell in a developing C. elegans embryo.
Figure 12B:
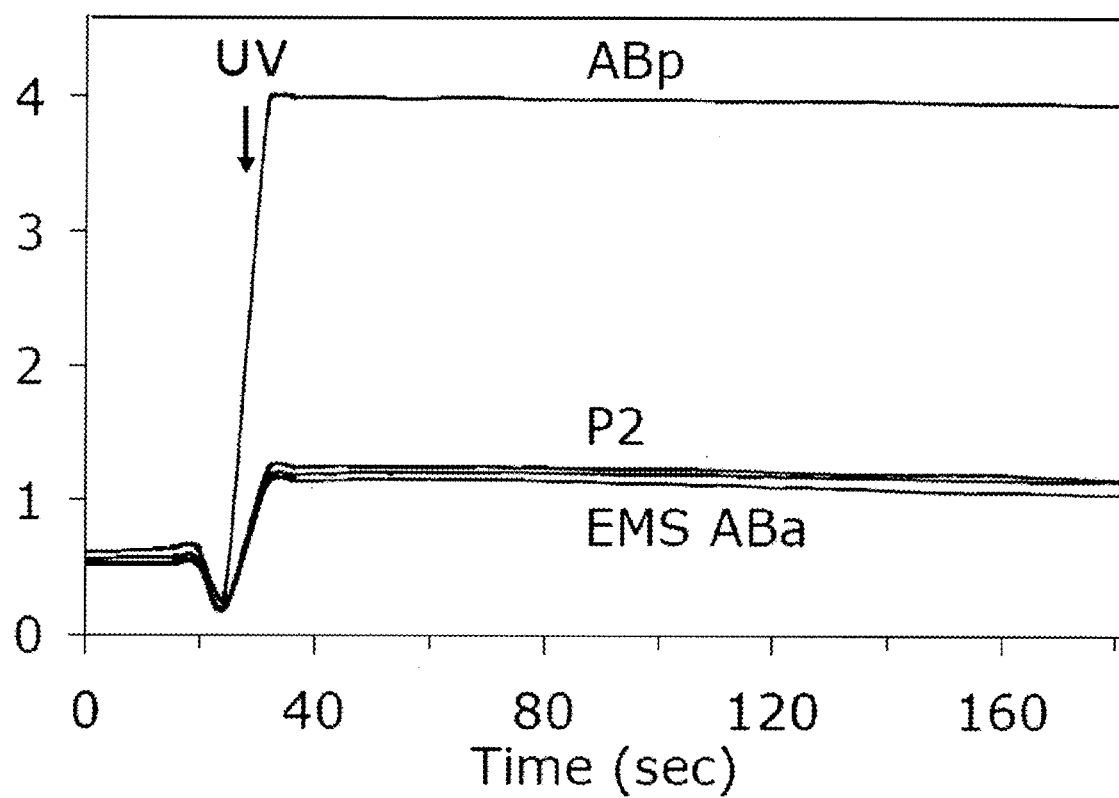

In another set of control experiments, a type I dextran conjugate of a caged coumarin, dextran-HCC-NPE, which does not release the dye from the carrier was photolyzed. The type I dextran conjugate and the photolysis reaction are shown in FIG. 12(a), (1) (Ac)$_2$O/pyridine, (2) Dextran amine (10 KD), DIEA, DMSO; then dialysis. Uncaging dextran-HCC-NPE (type I) generated dextran-HCC (10 KD). This dextran-dye conjugate was not expected to pass through gap junction channels because its molecular weight was above the typical molecular exclusion limit (about 1,500 Da) of connexin/innexin channels. Indeed, no movement of HCC-dextran (10 KD) to neighboring cells was observed after a local uncaging (FIG. 12(b)), further supporting that cell-cell transfer of free HCC in *C. elegans* embryos is mediated through gap junction channels. FIG. 12(b) shows the time course of average dextran-HCC fluorescence intensity of the bulk cytoplasm. The results are representative of four uncaging experiments for each condition.

EXAMPLE 7

Imaging Cell Coupling in Living Worms

To determine if dextran-CANPE-HCC can be retained inside cells throughout embryonic development, the probe was uncaged in hatched larvae. Single cell uncaging of dextran-CANPE-HCC in living worms was carried out with a MicroPoint Laser System (Photonic Instruments, St. Charles, Ill.) installed on the Axiovert 200M microscope, using a nitrogen UV laser (Model NL100, Stanford Research Systems, Sunnyvale, Calif.) and a BPBD dye cell to provide laser output at 364 nm for uncaging. When imaging worms, 1-phenoxy-2-propanol (0.1% in water) was added to the agar pad to reduce the worms' movements.

Figure 13:
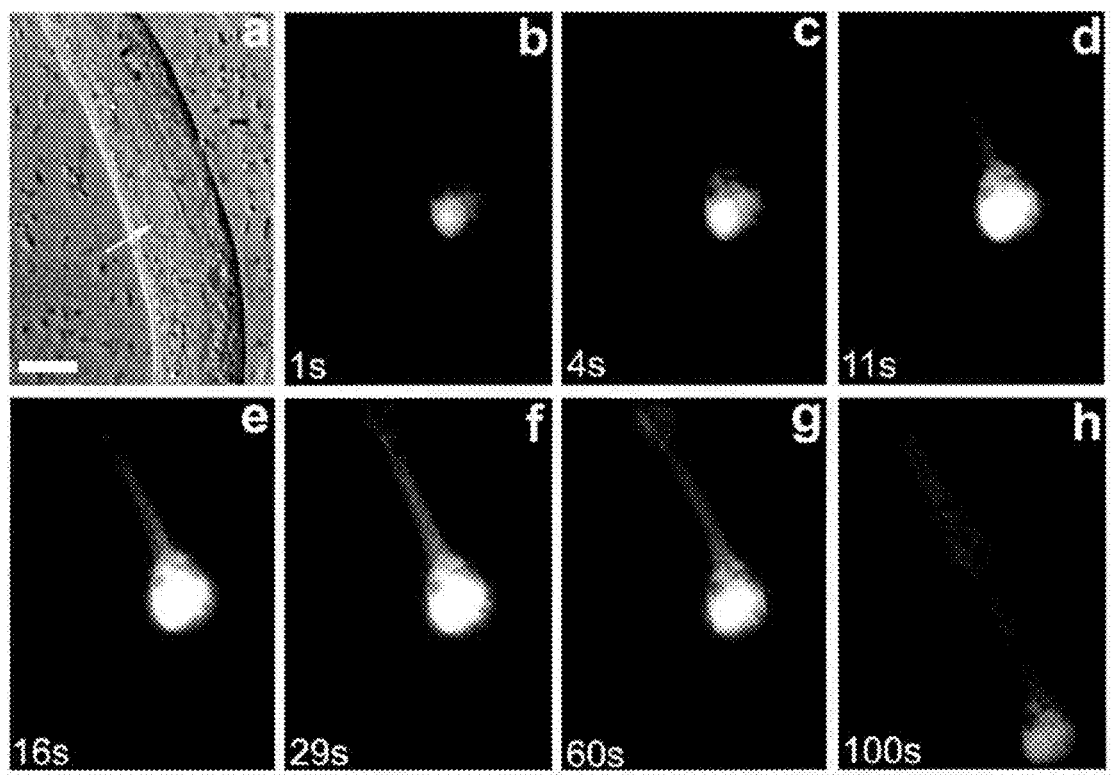
FIG. 13 shows dye transfer in the pharynx of C. elegans larvae. (a) DIC image. The laser uncaging spot was positioned within the terminal bulb (indicated by the arrow). Scale bar=10 μm. (b-g) Coumarin fluorescence images after local uncaging of the terminal bulb. Time (sec) elapsed after the first uncaging is indicated. Additional UV pulses were delivered at 4, 11, and 16 sec (c-e). (h) Coumarin fluorescence image of the same larva after moving the stage of the microscope to fit the entire pharynx into the viewing area of a CCD camera.

In both L1 and L2 stage larvae, global uncaging of dextran-CANPE-HCC generated intense coumarin signal throughout the animal. To examine dye transfer in live animals, local photo-uncaging experiments were performed in the pharynx of young larvae. The pharynx of *C. elegans* consists of eight groups of muscle cells, pharyngeal muscles 1 to 8. Neighboring pharyngeal muscle cells are connected by gap junction channels. To uncage dextran-CANPE-HCC, a UV laser (365 nm) was focused at the posterior terminal bulb, approximately where group 7 pharyngeal muscles reside. FIG. 13 shows the results. Additional UV pulses were delivered at 4, 11, and 16 sec. Upon delivering laser pulses, HCC fluorescence immediately rose in the irradiated area and the dye rapidly spread towards the anterior of pharynx. Additional UV pulses were delivered at 4, 11 and 16 sec. In just about 11 seconds, HCC could be clearly observed throughout the isthmus. By about 30 seconds, coumarin signal could be seen in the metacarpus. The photoactivated dye continued to diffuse along pharyngeal muscle cells towards the tip of procorpus, and it nearly filled the entire pharynx in about 100 seconds. During the experiment, the worm was alive and showed some minor movements sporadically.

Figure 14:
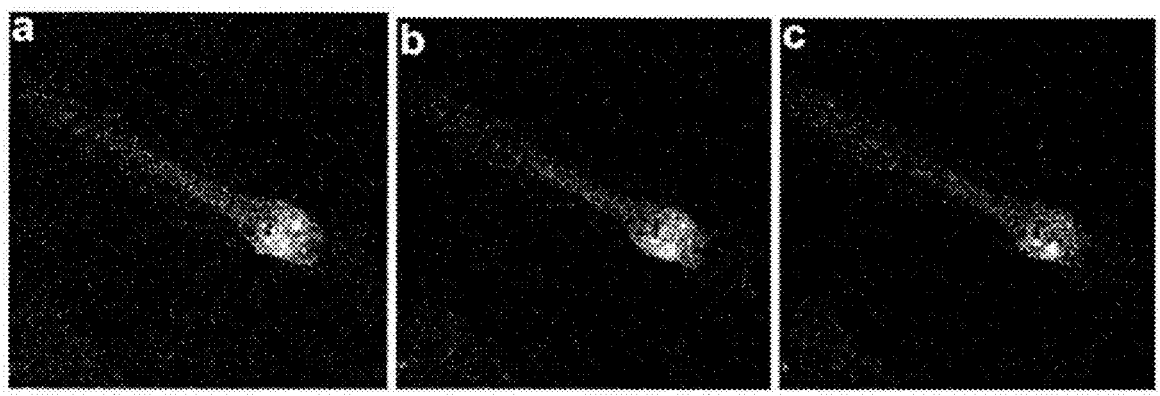
FIG. 14 shows two photon uncaging and imaging of dextran-CANPE-HCC. A L1 larva labeled with dextran-CANPE-HCC was photolyzed at the posterior terminal bulb by two photon excitation at 740 nm (~10 mW, ~15 msec). After two photon uncaging, the excitation wavelength was changed to 820 nm before starting to image coccmarin signal. The process of switching the excitation wavelength from 740 nm took about 20 seconds. Images were taken at ~21 sec (a), ~40 sec (b), and ~80 sec (c) after two photon uncaging.

Since dextran-CANPE-HCC has high two photon uncaging efficiency, and because HCC is a good fluorophore for two photon imaging, the technique of two photon excitation was also applied to monitor cell coupling in L1 larva of *C. elegans*. Two photon uncaging and imaging were performed on a LSM 510 imaging system (Carl Zeiss) equipped with a Chameleon-XR laser (Coherent). The laser power was set below 20 mW at the entrance of the scanning head as measured by a power meter (FieldMate, PM10 sensor, Coherent). The incident laser power at the specimen, estimated by placing the power meter just above the objective, was about half of the value measured at the entrance of the scan head. To uncage Dextran-CANPE-HCC, an area of the posterior terminal bulb was raster-scanned at 740 nm briefly (about 10 mW, about 15 msec). Afterwards the excitation wavelength was switched to 820 nm to image HCC fluorescence by two photon excitation (Dakin and Li, 2006). The process of switching the excitation wavelength from 740 nm to 820 nm took about 20 seconds. Subsequent two photon imaging of released HCC by exciting at 820 nm showed similar dye diffusion as UV uncaging experiments. Results are shown in FIG. 14. Images were taken at about 21 sec (a), about 40 sec (b), and about 80 sec (c) after two photon uncaging. Integrating two photon uncaging and imaging techniques maximizes the spatial selectivity of two photon excitation, and is most useful in examining cell coupling in three dimensions when UV uncaging fails to provide sufficient selectivity to mark cells of interest.

EXAMPLE 8

Measuring Potential UV Damage

To assess the potential UV damage to living embryos during uncaging, the whole labeled embryos were exposed to UV light for the same duration which was used for local uncaging. These embryos developed normally into adults and showed no observable behavioral defects (n=10 embryos). Moreover, even when the UV dose was increased by ten times, no abnormalities were observed in the embryos or in the adults (n=10 embryos). The treated worms showed usual morphology, moved and fed normally, and laid many embryos. This suggests that the amount of UV light required for uncaging dextran-CANPE-HCC is well below the UV dose that may harm cells or perturb embryonic development.

REFERENCES CITED

The entire content of each of the following cited reference is hereby incorporated by reference.

Bao, Z.; Murray, J. I.; Boyle, T.; Ooi, S. L.; Sandel, M. J.; Waterston, R. H. *Proc Natl Acad Sci USA* 2006.

Bossinger, O.; Schierenberg, E. *Dev Biol* 1992, 151, 401-9.

Bossinger, O.; Schierenberg, E. *Int J Dev Biol* 1996, 40, 431-9.

Brenner, S. *Genetics* 1974, 77, 71-94.

Dakin, K.; Zhao, Y. R.; Li, W. H. *Nature Methods* 2005, 2, 55-62.

Dakin, K.; Li, W. H. *Nat Methods* 2006, 3, 959.

Mitchison, T. J.; Sawin, K. E.; Theriot, J. A.; Gee, K.; Mallavarapu, A. *Methods Enzymol* 1998, 291, 63-78.

Nagayama, S.; Zeng, S.; Xiong, W.; Fletcher, M. L.; Masurkar, A. V.; Davis, D. J.; Pieribone, V. A.; Chen, W. R. *Neuron* 2007, 53, 789-803.

Rozental, R.; Srinivas, M.; Spray, D. C. In *Connexins methods and protocols*; Bruzzone, R., Giaume, C., Eds.; Humana Press: Totowa, 2001, p 447-476.

Squirrell, J. M.; Wokosin, D. I,.; White, J. G.; Bavister, B. D. *Nat Biotechnol* 1999, 17, 763-7.

Zhao, Y.; Zheng, Q.; Dakin, K.; Xu, K.; Martinez, M. L.; Li, W. H. *J Am Chem Soc* 2004, 126, 4653-63.

What is claimed is:

1. A composition comprising a macromolecular carrier, a protecting group, and a coumarin fluorophore, and having the general structure:

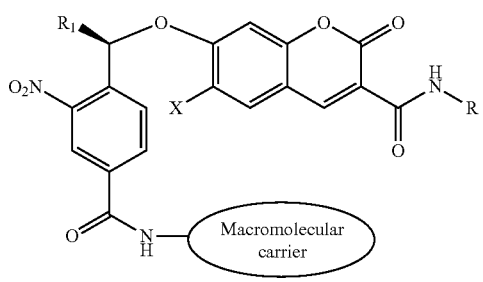

wherein:

X is H, F, Cl, or Br;

$R_1$ is H or $CH_3$;

R is one substituted or unsubstituted amino acid or a peptide containing up to 20 substituted or unsubstituted amino acids either in D or L configuration any linear or branched alkyl chain up to 20 carbon atoms, oligonucleotide containing amino groups at either 5' or 3' terminal, a therapeutic drug, a neurotransmitter, a molecule containing amino or carboxylate groups, or a combination thereof; and the macromolecular carrier is a protein, antibody, dextran amine, polylysine, polyethylene glycol, dendrimer, nanoparticle, quantum dot, a macromolecule containing one or more amino or thiol groups, or a combination thereof.

2. A composition of a photoactivatable dye comprising:

a macromolecule;

a bifunctional photolabile protecting group; and a coumarin fluorophore, wherein the macromolecule is linked to the coumarin fluorophore through the protecting group, wherein the bifunctional photo labile protecting group is linked to a 7-hydroxy group of the coumarin fluorophore, wherein the macromolecule is a biomolecule.

3. The composition of claim 2, wherein the macromolecule is dextran.

4. The composition of claim 2, wherein the protecting group is 1-(4-carbamoyl-2-nitrophenyl)ethyl.

5. The composition of claim 2, wherein the coumarin fluorophore is 7-hydroxycoumarin 3-carboxamide.

6. The composition of claim 2, having the following structure:

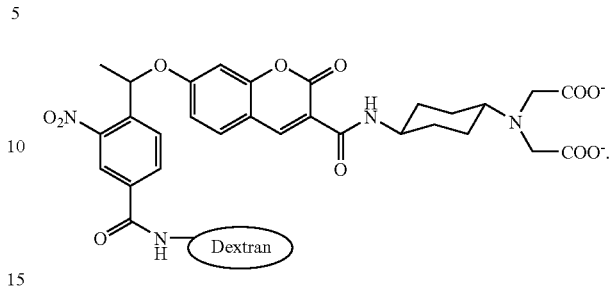

7. A composition comprising a biomolecule, a protecting group, and a coumarin fluorophore, and having the general structure:

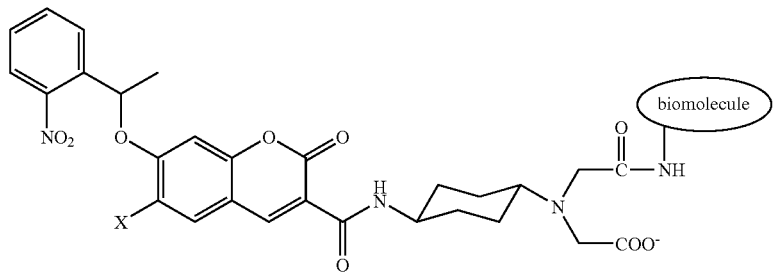

wherein X is H, F, Cl, or Br, and the a macromolecule is a protein, antibody, dextran amine, polylysine, polyethylene glycol, dendrimer, nanoparticle, quantum dot, a macromolecule containing one or more amino or thiol groups, or a combination thereof.

8. A method for using fluorescence to observe cell-cell coupling and cell-cell communication in a living animal, comprising:

injecting the animal with the composition of claim 1 to produce a labeled animal;

directing a light source with a first selected wavelength to the labeled animal at a region of interest to produce a first region of fluorescence; and observing the first region of fluorescence.

9. The method of claim 8, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

10. The method of claim 8, further comprising the step of directing a light source with a second selected wavelength to the labeled animal at the region of interest to produce a second region of fluorescence and observing the second region of fluorescence.

11. A method for using fluorescence to observe patterns of junctional cell coupling in cells of interest, comprising:

injecting at least one of the cells of interest with the composition of claim 1 to produce at least one labeled cell;

directing a light source with a first selected wavelength to the at least one labeled cell at a region of interest to produce a first region of fluorescence; and observing the first region of fluorescence.

12. The method of claim 11, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

13. The method of claim 11, wherein the cells of interest are cells of developing embryos.

14. The method of claim 11, further comprising the steps of directing a light source with a second selected wavelength to the at least one labeled cell at the region of interest to produce a second region of fluorescence and observing the first region of fluorescence.

15. A method for using fluorescence to observe cell-cell coupling and cell-cell communications in developing embryos and young animals produced by adult parent animals, comprising:
   injecting the composition of claim 1 into reproductive cells of the adult parent animals to produce labeled reproductive cells;
   allowing the adult parent animals to produce embryos with the labeled reproductive cells, wherein the embryos are labeled with the composition of claim 1;
   directing a light source with a first selected wavelength to at least one cell of the embryos at a region of interest to produce a first region of fluorescence; and
   observing the first region of fluorescence as the embryos develop into young animals.

16. The method of claim 15, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

17. The method of claim 15, further comprising the steps of directing a light source with a second selected wavelength to the at least one cell of the embryos at the region of interest to produce a second region of fluorescence and observing the second region of fluorescence as the embryos develop into young animals.

18. A method for comparing the coupling strength between pairs of coupled cells, one cell of each pair being a donor cell and one being a recipient cell, comprising:
   injecting the composition of claim 1 into the donor cells to produce labeled donor cells;
   directing a light source with a selected wavelength to the labeled donor cells to produce regions of fluorescence;
   measuring increases in fluorescence intensity in the recipient cells as a function of time;
   calculating slopes of the increases in fluorescence intensity in the recipient cells as a function of time; and
   comparing the slopes of the increases in fluorescent intensity to determine which pairs of coupled cells had greater coupling strength.

19. The method of claim 18, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

20. A method for using fluorescence to trace lineage of cells of interest, comprising:
   injecting at least one of the cells of interest with the composition of claim 1 to produce at least one labeled cell;
   allowing the at least one labeled cell to produce labeled progeny cells;
   directing a light source with a first selected wavelength to the at least one labeled cell and the labeled progeny cells to produce a first region of fluorescence; and
   observing the first region of fluorescence.

21. The method of claim 20, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

22. The method of claim 20, wherein the cells of interest are cells of developing embryos.

23. The method of claim 20, further comprising the steps of directing a light source with a second selected wavelength to the at least one labeled cell and the labeled progeny cells to produce a second region of fluorescence and observing the second region of fluorescence.

24. A method for using fluorescence to track molecular movements in cells of interest, comprising:
   injecting the composition of claim 1 into the cells of interest to produce labeled cells;
   directing a light source with a first selected wavelength to the labeled cells to produce a first region of fluorescence; and
   observing the first region of fluorescence.

25. The method of claim 24, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

26. The method of claim 24, further comprising the steps of directing a light source with a second selected wavelength to the labeled cells to produce a second region of fluorescence and observing the second region of fluorescence.

27. A method for using fluorescence to trace lineage of cells of interest, comprising:
   injecting at least one of the cells of interest with the composition of claim 7 to produce at least one labeled cell;
   allowing the at least one labeled cell to produce labeled progeny cells;
   directing a light source with a first selected wavelength to the at least one labeled cell and the labeled progeny cells to produce a first region of fluorescence; and
   observing the first region of fluorescence.

28. The method of claim 27, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

29. The method of claim 27, wherein the cells of interest are cells of developing embryos.

30. The method of claim 27, further comprising the steps of directing a light source with a second selected wavelength to the at least one labeled cell and the labeled progeny cells to produce a second region of fluorescence and observing the second region of fluorescence.

31. A method for using fluorescence to track molecular movements in cells of interest, comprising:
   injecting the composition of claim 7 into the cells of interest to produce labeled cells;
   directing a light source with a first selected wavelength to the labeled cells to produce a first region of fluorescence; and
   observing the first region of fluorescence.

32. The method of claim 31, wherein the composition comprises a macromolecule that is dextran, a protecting group that is 1-(4-carbamoyl-2-nitrophenyl)ethyl, and a coumarin fluorophore that is 7-hydroxycoumarin 3-carboxamide.

33. The method of claim 31, further comprising the steps of directing a light source with a second selected wavelength to the labeled cells to produce a second region of fluorescence and observing the second region of fluorescence.

* * * * *